US012245941B2

United States Patent
Rafiee et al.

(10) Patent No.: US 12,245,941 B2
(45) Date of Patent: Mar. 11, 2025

(54) CARDIAC ANNULOPLASTY PROCEDURES, RELATED DEVICES AND METHODS

(71) Applicant: Transmural Systems LLC, Andover, MA (US)

(72) Inventors: Nasser Rafiee, Andover, MA (US); Stuart Macdonald, Andover, MA (US); Koosha Rafiee, Andover, MA (US)

(73) Assignee: Transmural Systems LLC, Andover, MA (US)

( * ) Notice: Subject to any disclaimer, the term of this patent is extended or adjusted under 35 U.S.C. 154(b) by 1110 days.

(21) Appl. No.: 17/086,360

(22) Filed: Oct. 31, 2020

(65) Prior Publication Data

US 2021/0045879 A1 Feb. 18, 2021

Related U.S. Application Data

(63) Continuation of application No. PCT/US2020/045675, filed on Aug. 10, 2020.

(60) Provisional application No. 62/884,582, filed on Aug. 8, 2019.

(51) Int. Cl.
*A61F 2/24* (2006.01)

(52) U.S. Cl.
CPC .......... *A61F 2/2466* (2013.01); *A61F 2/2445* (2013.01); *A61F 2210/0014* (2013.01); *A61F 2250/0098* (2013.01)

(58) Field of Classification Search
CPC ...... A61F 2/2442; A61F 2/2451; A61F 2/246; A61F 2/2466
See application file for complete search history.

(56) References Cited

U.S. PATENT DOCUMENTS

| 6,144,879 | A | 11/2000 | Gray |
| 9,610,159 | B2 | 4/2017 | Christianson et al. |
| 9,636,505 | B2 | 5/2017 | Sanghera et al. |
| 10,610,354 | B2 | 4/2020 | Vidlund et al. |
| 2006/0281968 | A1 | 12/2006 | Duran et al. |
| 2010/0324668 | A1 | 12/2010 | Maurer et al. |
| 2016/0213472 | A1 | 7/2016 | Kim |
| 2017/0119489 | A1 | 5/2017 | Kim |
| 2017/0312078 | A1 | 11/2017 | Krivoruchko |
| 2018/0098850 | A1 | 4/2018 | Rafiee et al. |
| 2020/0229824 | A1 | 7/2020 | Kim et al. |

FOREIGN PATENT DOCUMENTS

| CN | 105555231 B | 2/2018 |
| KR | 20150026766 A | 3/2015 |
| WO | 2021026541 A1 | 2/2021 |

OTHER PUBLICATIONS

International Search Report for Application No. PCT/US2020/045675 dated Nov. 12, 2020.

(Continued)

*Primary Examiner* — William H Matthews
(74) *Attorney, Agent, or Firm* — DeWitt LLP; Brian R. Pollack, Esq.

(57) ABSTRACT

Devices and methods are disclosed for the treatment or repair of regurgitant cardiac valves, such as a mitral valve and/or tricuspid valve. An illustrative annuloplasty device can be placed in the coronary sinus to reshape the mitral valve and reduce mitral valve regurgitation as well as tricuspid regurgitation. The disclosure also provides improved techniques for cardiac pacing.

16 Claims, 30 Drawing Sheets

(56) References Cited

OTHER PUBLICATIONS

Written Opinion of the International Searching Authority for Application No. PCT/US2020/045675 dated Nov. 12, 2020.
Yong-Hyun Park et al. Mitral Loop Cerclage Annuloplasty for Secondary Mitral Regurgitation. [online] Cardiovascular Interventions. vol. 10, No. 6, 2017.
European Search Report Mailed Aug. 30, 2023 in co-pending European Patent Application No. 20849669.
Park Yong-Hyun et al. "Mitral Loop Cerclage Annuloplasty for Secondary Mitral Regurgitation", JACC Cardiovascular Interventions, vol. 10 No. 6, Mar. 1, 2017, pp. 597-610.

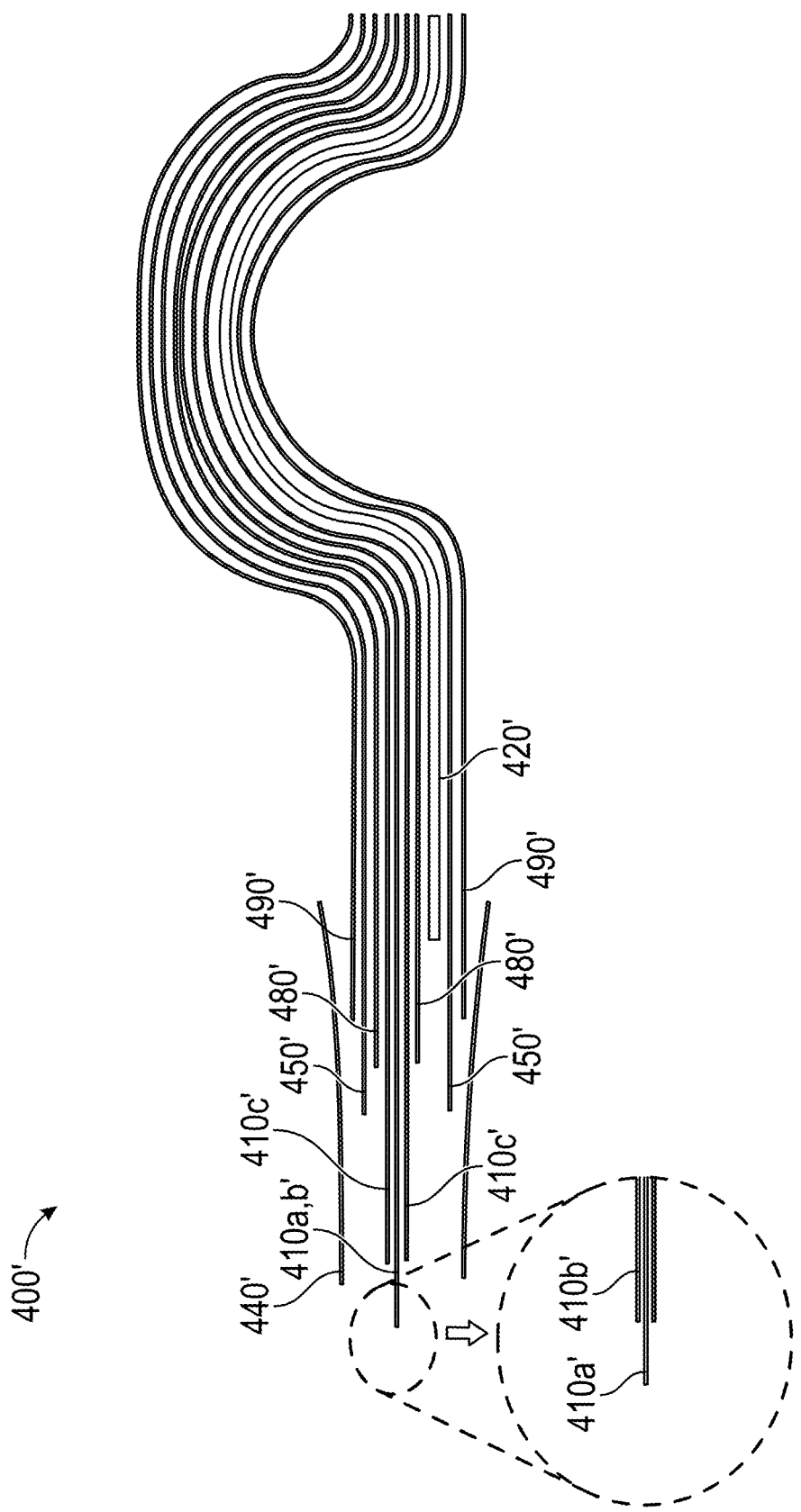

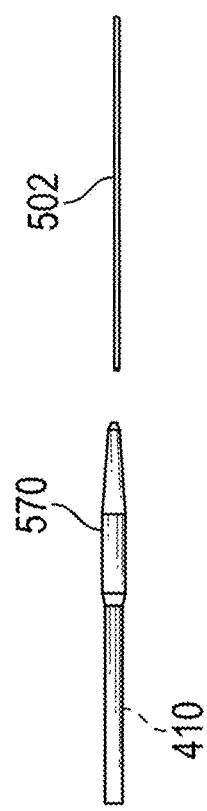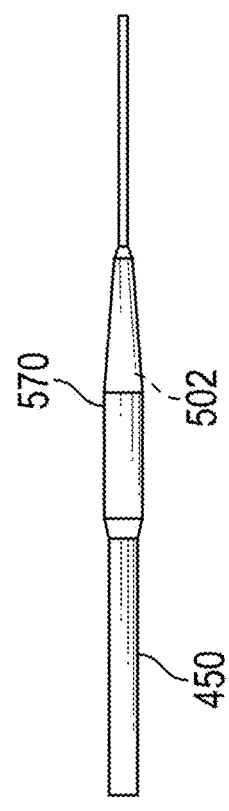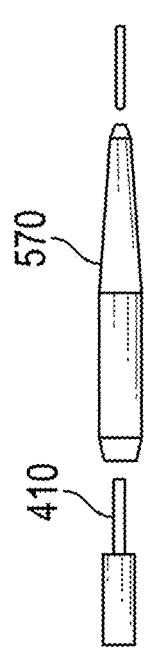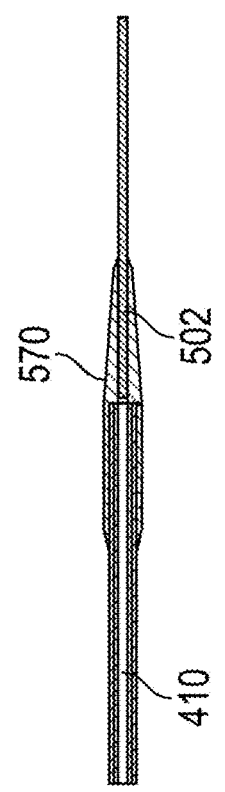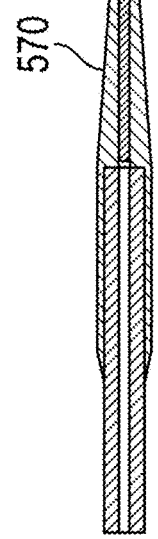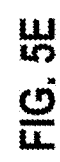

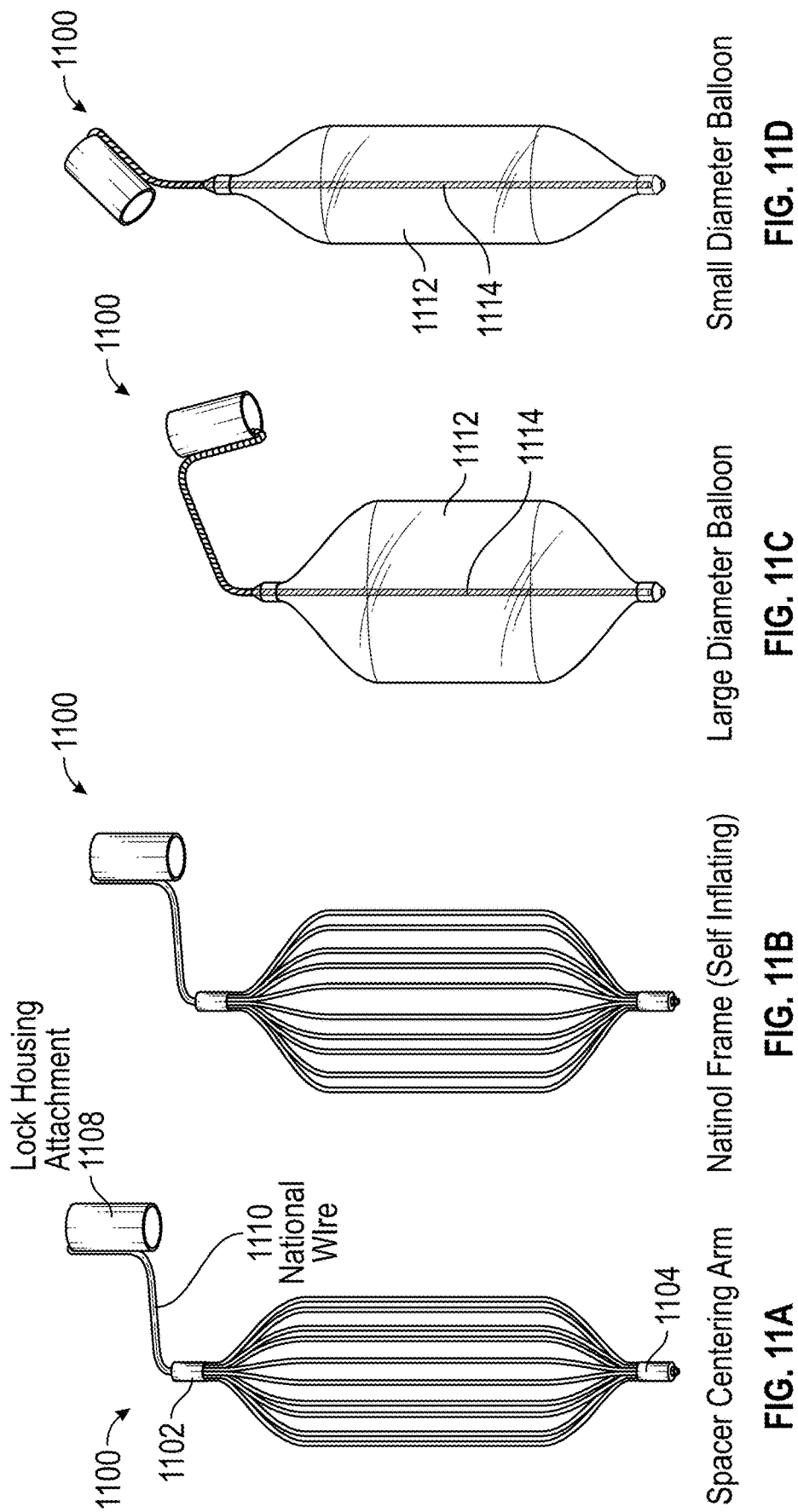

Spacer on Wishbone Lock

Wishbone and Lock - With Saddle

Wishbone and Lock - No Saddle

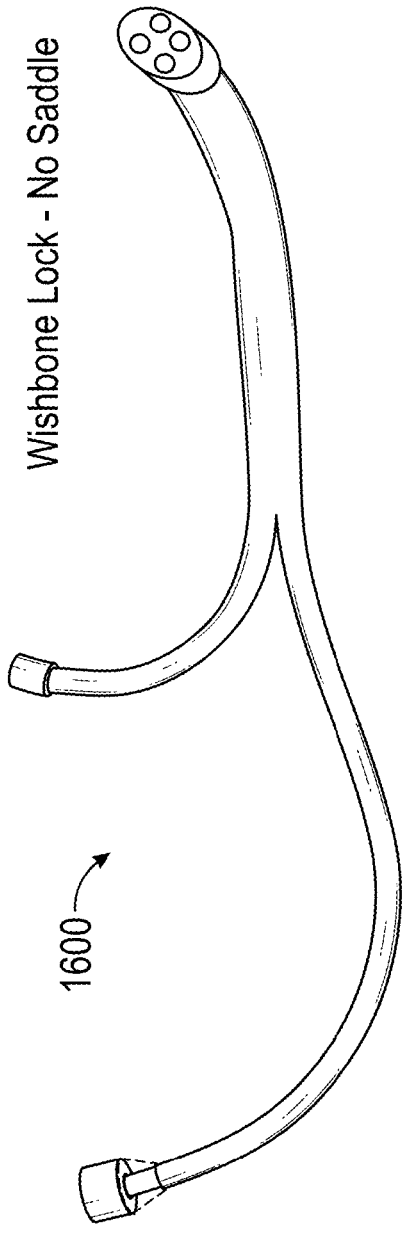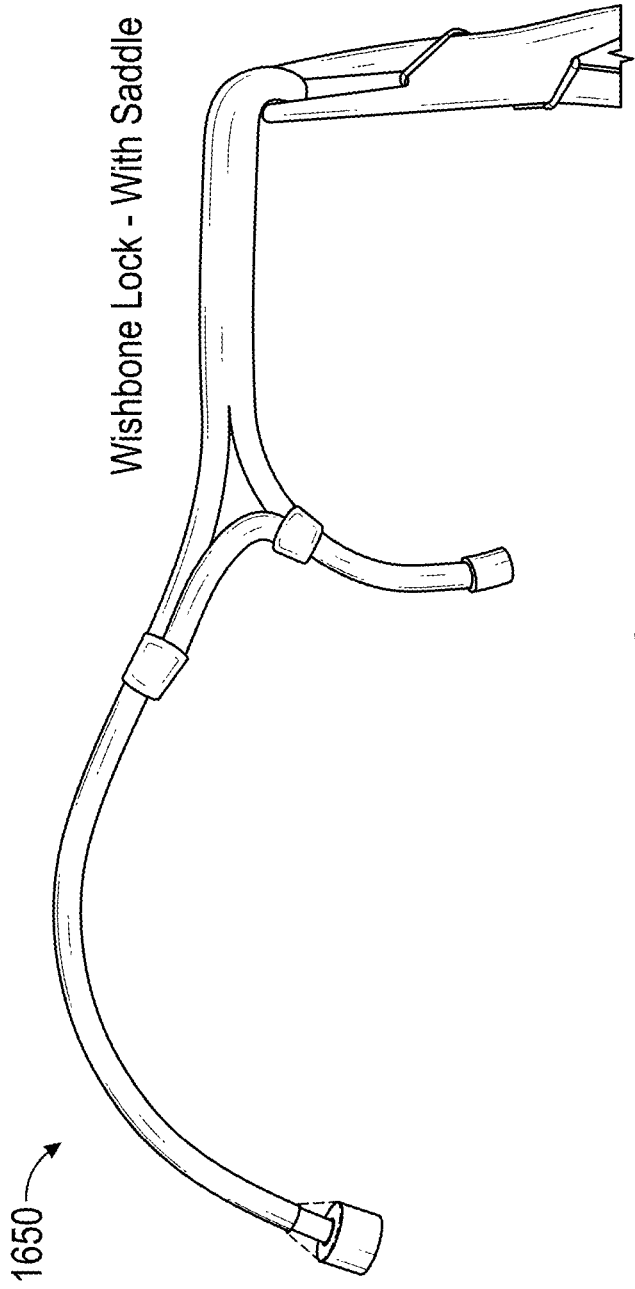
FIG. 16A — Wishbone Lock - No Saddle
FIG. 16B — Wishbone Lock - With Saddle

CARDIAC ANNULOPLASTY PROCEDURES, RELATED DEVICES AND METHODS

CROSS-REFERENCE TO RELATED APPLICATIONS

This patent application is a continuation of and claims the benefit of priority to International Application No. PCT/US20/45675, filed Aug. 10, 2020, which is related to and claims the benefit of priority to U.S. Provisional Application Ser. No. 62/884,582, filed Aug. 8, 2019. This patent application is also related to patent application Ser. No. 15/796,344, filed Oct. 27, 2017, now U.S. Pat. No. 10,433,962 and U.S. patent application Ser. No. 16/264,531, filed Jan. 31, 2019. The disclosure of each of the foregoing patent applications is expressly incorporated by reference herein for any purpose whatsoever.

FIELD OF THE DISCLOSURE

The present disclosure relates to techniques and devices in which implants are disposed in the heart to alter the structure and/or function of the heart.

BACKGROUND

Traditional mitral valve annuloplasty requires open heart surgery with a sternotomy or thoracotomy and cardiac arrest and cardio-pulmonary bypass. For example, the annuloplasty procedure is performed through a surgical incision in which the effective size of the valve annulus is reduced by attaching a prosthetic annuloplasty ring to the left atrial aspect of the mitral valve annulus. A variety of rigid and flexible annuloplasty rings have been developed for this purpose, such as those shown in U.S. Pat. Nos. 4,917,698; 5,041,130; 5,061,277; 5,064,431; 5,104,407; 5,201,880; and 5,350,420. Although very effective, this open-heart procedure is accompanied by substantial morbidity and prolonged convalescence. As a result, the procedure often is not offered to patients who are insufficiently symptomatic to justify the surgical risk and morbidity, or to patients who suffer advanced disease, or to patients with substantial co-morbidity.

Percutaneous approaches to mitral valve repair have been developed to reduce the clinical disadvantages of the open-heart procedures. But, these procedures suffer from various drawbacks. International Application No. PCT/US2017/031543, filed May 8, 2017, related to the present disclosure, presents considerable improvements over the state of that prior art. In some aspects, the present disclosure provides still further improvements over the prior art.

In other aspects, the present disclosure provides improvements in the area of pacing. Since a pacemaker was first introduced by Furman and Rovinson in 1958, the pacemaker has been used as an important device for treating patients with bradyarrhythmia. Pacemakers are usually used in treatments for arrhythmia such as complete atrioventricular block, high degree atrioventricular block, and sinus node dysfunction accompanied by symptoms. A treatment using a pacemaker is a method that artificially provides an electrical stimulus when an electrical stimulus is not normally transmitted to a heart, and/or when an incorrect stimulus is transmitted to the heart.

FIGS. 1A-1C are views of a conduction system of a human heart, in which FIG. 1A shows a flow in a conduction system, FIG. 1B shows a waveform in an electrocardiogram, and FIG. 1C illustrates the relationship between a conduction process and a waveform. As discussed in U.S. patent application Ser. No. 15/328,046, filed Jun. 16, 2015 (incorporated by reference herein in its entirety for any purpose whatsoever), an electrical stimulus is transmitted to the overall ventricles through a conduction pathway after passing through a sinoatrial (SA) node, an atrioventricular (AV) node in the atriums and then passing through the bundle of His and a bundle branch in the ventricles.

In an electrocardiogram, a QRS-complex is generated by a depolarization process of ventricular muscles. The first downward wave following a P-wave is called a Q-wave, the first upward wave is called an R-wave, and the downward wave following the R-wave is called an S-wave. The width of the QRS indicates the time taken for electricity to be conducted throughout the ventricles. The width of the QRS is typically within about 0.12 seconds (around about 90 ms) in a normal state, but when it is 0.12 seconds or more, it indicates the presence of an interventricular conduction defect.

A pacemaker is generally composed of a generator and a lead. The generator supplies power and includes a controller with processing circuitry as well as detection circuitry for detecting operational aspects of the heart. The pacemaker typically supplies power or suspends power, depending on the state of operation of the heart. Power is selectively applied to the heart by way of the lead, which terminates in an electrode. Pacemakers typically operate in a bipolar manner, meaning that the lead actually includes two electrodes—one for delivering electrons (anode) and one for absorbing electrons (cathode). However, the cathode is typically considered to be the hot lead for purposes of convention. In the event the anode breaks or ceases to function, the pacemaker controller will detect this and then operate the device as a monopolar device, wherein the anode becomes the casing and the "hot" lead continues to act as a cathode.

According to a common treatment that is performed by a pacemaker at present, the tip of the lead of a pacemaker is inserted and fixed in the apex of the right ventricle (RV apex) of ventricles and then electrical stimulus is provided. This is called right ventricular apical pacing (RVAP). In RVAP, the electrical stimulus at the RV apex is not transmitted through the conduction system of the heart that quickly transmits electrical stimulus in a ventricle. It is instead transmitted through cariomyocytes of the ventricle that relatively slowly transmit electrical stimulus. Consequently, it can take a relatively long time for the electrical stimulus to spread through the entire ventricle. This can be expected to (and typically does) result in an increase of QRS width, which results in ventricular desynchronization, and reduces the pumping efficiency of the heart. Ideally, the ventricles are contracted at the same time for better efficiency.

To address this, attempts have been made to position the electrode of the pacemaker lead at a right ventricular basal septum and applying electrical stimulus around the nerve bundles that precipitate ventricular contraction. This is referred to as right ventricular septal pacing (RVSP). The RVSP is most usually used at the interventricular septum of a right ventricular outflow tract (RVOT). RVSP theoretically compensates for the defects of the RVAP, but in the actual operation it is difficult to accurately position the lead of a pacemaker at the interventricular septum around the RVOT and the lead may be separated or moved, so the operation itself is difficult and accordingly it is not generally used. The RVSP has another characteristic that positions the lead tip at an interventricular septum, but stimulates not the inside, but the outer side of the interventricular septum, and it is known that the RVSP is less effective than the method of stimulating the endocardium or the center of an interventricular septum.

Another method of obtaining a narrower QRS is applied to a case when a patient with heart failure accompanied by ventricular insufficiency has a wide QRS in an electrocardiogram. This method uses two leads, and positions a lead at an RV apex and applies electrical stimulus and positions the other lead at a left lateral vein and applies electrical stimulus to a side of the left ventricle. This treatment seeks to obtain a narrower QRS by simultaneously applying electrical stimulus to the RV apex and the side of the left ventricle. This is referred to as "Cardiac Resynchronization Therapy (CRT)". CRT is a very effective treatment when a patient with heart failure has LBBB (left bundle branch block). However, CRT has a deficiency in that it needs to use two leads for stimulating ventricles in order to obtain a narrower QRS.

Intraseptal pacing that can apply direct electrical stimulus to an interventricular septum has been attempted. For example, methods by forcibly positioning the lead of a pacemaker into the interventricular septum directly through the left ventricle from the right ventricle have been disclosed in US2010/0298841 and US 2013/0231728. These methods have high invasion depth that causes an artificial loss of interventricular septum between the left and right ventricles, have a high possibility of tearing surrounding tissues during the operation, and have a high possibility of causing an embolism due to air or blood clots. Further, these methods have many dangers and limits, for example, it can locally approach the middle portion or the apex of ventricles rather than the base which is preferable. U.S. Ser. No. 15/328,046 attempts to improve on the state of the art by a further approach intended to address the deficiencies in the aforementioned approaches. The present disclosure provides additional improvements over the state of the art.

SUMMARY OF THE DISCLOSURE

In particular embodiments, the disclosure provides implementations of an implant that includes a tether formed into a loop shape, a lock slid over the tether and engaged with the tether to maintain tension in the tether, and a spacer coupled to the lock and extending from the implant, the spacer being configured to be disposed between leaflets of a cardiac valve to permit leaflets of the cardiac valve to coapt against the spacer.

In some implementations, the tether can include an elongate inner tether and an outer sheath material, wherein the tether includes radiopaque material along its length. The radiopaque material within the elongate inner tether can include a radiopaque wire disposed within a length of heat shrunk polymeric tube that resides within a hollow core of the elongate inner tether.

In some implementations, the spacer can include an inflatable member or self-expanding volume that expands to a predetermined size to occupy a portion of a patient's native tricuspid valve annulus. The spacer can include a plurality of self-expanding filaments having first and second ends at proximal and distal hubs that expand radially outwardly from a compressed configuration to occupy a volume in the right ventricular outflow tract. The spacer can include an elongate inflatable member configured to occupy a portion of a patient's RVOT in the region of the patient's tricuspid valve. The inflatable member can include a core member coupled to first and second ends of the inflatable member.

In some implementations, the spacer can be coupled to the implant by way of a spacer tether. The spacer tether can be coupled to the implant by way of a spacer lock that couples to the lock of the implant. The spacer can include a membrane about its outer periphery. The implant lock can define at least one distal opening therein, and the at least one distal opening can be connected to two distally extending tubular limbs disposed about the outer sheath material. A first of the tubular limbs can be configured to traverse the tricuspid valve and can include an atraumatic distal tip formed thereon for distributing axially applied stress across a surface of a native septum after traversing the tricuspid valve. The first tubular limb can be configured to permit the outer sheath material to pass therethrough. A second of the tubular limbs can be configured to traverse the coronary sinus and can be configured to permit the outer sheath material to pass therethrough.

The disclosure further provides a method of implanting an implant as described above. The method can include one or more of directing a distal end of a guidewire at least partially through a coronary sinus of a heart and into the right ventricle or the right atrium, withdrawing the distal end of the guidewire from the patient such that the proximal and distal ends of the guidewire are outside the patient, and the guidewire traverses a loop shaped path through the heart by way of the coronary sinus to surround a native mitral valve, crimping a crimp of an implant according to claim 1 to a proximal end of the guidewire, advancing the implant until both ends of the outer sheath material are externalized from the patient, and fixating the implant in place to maintain the length of the sheath by advancing the lock along opposing ends of the outer sheath material, through the patient's vasculature and into the patient's heart, wherein the lock is fastened within the patient's heart. The method can further include one or more of advancing the spacer over the ends of the outer sheath material, disposing the spacer over the lock, disposing the spacer in the RVOT in the region of the tricuspid valve, and expanding the spacer in the patient's tricuspid valve to mitigate tricuspid valve regurgitation.

The disclosure further provides implementations of an implant that includes an elongate tether formed into a loop shape, an implant lock slid over the outer sheath and engaged with the outer sheath to maintain tension in the outer sheath material, wherein the implant lock defines at least one distal opening therein, said at least one distal opening being connected to two distally extending tubular limbs disposed about the outer sheath material and a saddle joining proximal end regions of the tubular limbs near the implant lock the saddle being configured to distribute stresses over cardiac tissue when the implant is under tension.

If desired, the saddle can be a band of material that urges against cardiac tissue when the implant is under tension. The saddle can be joined to the tubular limbs at least in part by way of a suture wrap. The saddle can be joined to the tubular limbs at least in part by way of shrink tubing. The saddle can be joined to the tubular limbs at least in part by way of at least partially melting material of the tubular limbs.

The disclosure further provides implementations of an implant that includes an elongate tether formed into a loop shape, and an implant lock slid over the outer sheath and engaged with the outer sheath to maintain tension in the outer sheath material. The implant lock can define at least one distal opening therein. The at least one distal opening can be connected to two distally extending tubular limbs disposed about the outer sheath material. A first of the tubular limbs can be configured to traverse the coronary sinus and can be configured to permit the elongate tether to pass therethrough. A second of the tubular limbs can be configured to traverse the tricuspid valve and configured to permit the elongate tether to pass therethrough. The first and second tubular limbs can be parallel to one another when they exit the lock along a first direction. The first of the tubular limbs can curves away from the first direction and the second tubular limb can continue to extend along the first direction away from a point of bifurcation from the first tubular limb. The second tubular limb can then curve along a parallel path to the first tubular limb, such that both tubular limbs point along the same direction generally orthogonal to the first direction.

The implant can further include a saddle joining the tubular limbs near the point of bifurcation. The saddle can be configured to distribute stresses over cardiac tissue when the implant is under tension. The saddle can be joined to the tubular limbs at least in part by way of a suture wrap. The saddle can be joined to the tubular limbs at least in part by way of shrink tubing. The saddle can be joined to the tubular limbs at least in part by way of at least partially melting material of the tubular limbs.

The disclosure further provides an implantable pacing system configured and arranged to circumnavigate a loop in a heart. The system includes an implant as described herein for performing a mitral cerclage procedure, at least one electrical conductor, a cardiac pacing controller including a power source, a pulse generator, and control circuitry operably coupled to the at least one electrical conductor, and at least one cardiac pacing electrode configured and arranged to be implanted in cardiac tissue, the at least one cardiac pacing electrode being electrically coupled to the cardiac pacing controller by way of the at least one electrical conductor.

If desired, the lock can be coupled to the cardiac pacing controller. The at least one electrical conductor is disposed at least partially within the elongate inner tether or outer sheath material. The lock can include the cardiac pacing lead routed therethrough. Electrical communication can be established with the cardiac pacing lead by engaging a portion of the lock. Electrodes can be placed along one or more of the tubular limbs of the implant or the saddle portion of the implant. If desired, the system can include a protective bridge for spanning the LCx artery when in the coronary sinus near the septal wall. The system can further include at least one sensor module that is at least partially disposed within the outer sheath, the at least one sensor module including at least one sensor for sensing at least one biological parameter. The at least one sensor module can include at least one pressure sensor for detecting blood pressure. The at least one sensor module can include at least one of: a chemical sensor, a distance sensor, a sensor having circuitry to detect electro physiological data, a movement sensor, and a location sensor.

If desired, the pacing system can further include at least one pacing lead. The at least one pacing lead can be configured and arranged to interface with the Right Atrium. The at least one pacing lead can be configured and arranged to interface with the Right Ventricle. The at least one pacing lead can be configured and arranged to interface with the Cardiac Vein. The at least one pacing lead can be configured and arranged to interface with tissue near the septal vein. The controller can be configured and arranged to provide at least one of pacing, defibrillation, measurement and control. The inner elongate tether, if provided, can include a loop antenna that conducts signals to and from the controller. If desired, the pacing system can further include a reservoir for containing a beneficial agent coupled to a dispenser controlled by the controller. The beneficial agent can include a medication. The beneficial agent can include a gene therapy material.

The disclosure further providers implementations of an implant that includes an elongate tether formed into a loop shape, an implant lock slid over the outer sheath and engaged with the outer sheath to maintain tension in the outer sheath material. The implant lock can define at least one distal opening therein. The at least one distal opening can be connected to at least one distally extending tubular limb disposed about the outer sheath material. The at least one distally extending tubular limb can be configured to traverse the tricuspid valve and be configured to permit the elongate tether to pass therethrough. The implant can further include a deployable leaflet coupled to the at least one distally extending tubular limb. The deployable leaflet can include at least one deployable structural rib having a first end coupled to the limb and a second free end, the at least one deployable structural rib being coupled to a membrane, the leaflet being configured to self-deploy into the RVOT upon installation and coapt with at least one tricuspid valve leaflet. If desired, the deployable leaflet can include a first deployable structural rib coupled to and extending from a distal end region of the at least one distally extending tubular limb, and a second deployable structural rib coupled to and extending from a proximal end region of the at least one distally extending tubular limb.

It is to be understood that both the foregoing general description and the following detailed description are exemplary and are intended to provide further explanation of the embodiments disclosed herein.

The accompanying drawings, which are incorporated in and constitute part of this specification, are included to illustrate and provide a further understanding of the method and system of the disclosure. Together with the description, the drawings serve to explain the principles of the disclosed embodiments.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIG. 3A is a left lateral external perspective view of the heart showing the lateral coronary artery branching from the ascending aorta, the branch of the lateral circumflex artery, and the great cardiac vein.

FIG. 3B is an enlarged view of a section of the arteries showing the coronary sinus crossing superficial to the left circumflex coronary artery at the level of the great cardiac vein.

FIG. 3C is a view similar to FIG. 3B but showing placement of a ligature (for example, and without limitation, a wire or suture) during annuloplasty without the protective device in place. When the ligature is tightened during the annuloplasty procedure, pressure is exerted on the branch of the coronary artery, restricting blood flow and myocardial perfusion.

FIG. 3D is an enlarged view of this same structure showing placement of the protective device over the ligature within the coronary sinus superficial to the coronary artery.

FIG. 4C is a cross-sectional schematic view of an illustrative implant in accordance with the present disclosure.

FIGS. 4E-4F are views of a further embodiment of an implant in accordance with the present disclosure.

FIGS. 5A-5E illustrate various aspects of a crimp in accordance with the present disclosure used to connect a distal end of an illustrative implant to a proximal end of a guide wire that has been directed through a patient's vasculature.

FIGS. 6A-6B are illustrations of target wires for use with the snare catheter of FIG. 6A.

FIGS. 11A-11E illustrate implementations of a spacer to be coupled to an implant in accordance with the disclosure.

FIGS. 16A-16B illustrate further implementations of implants in accordance with the present disclosure.

DETAILED DESCRIPTION OF ILLUSTRATIVE EMBODIMENTS

Figure 1B:
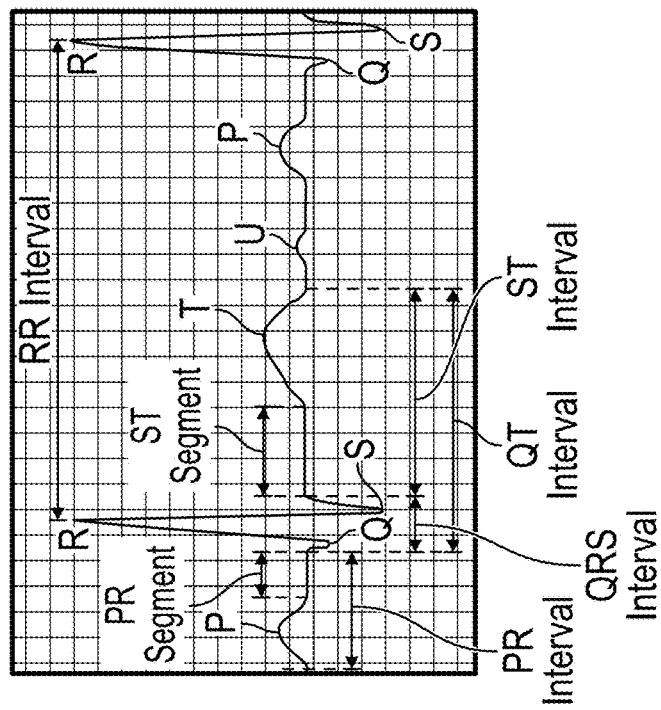
FIGS. 1A-1C illustrate aspects of cardiac pacing in accordance with the present disclosure.
Figure 1C:
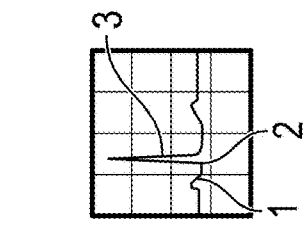
Figure 1A:
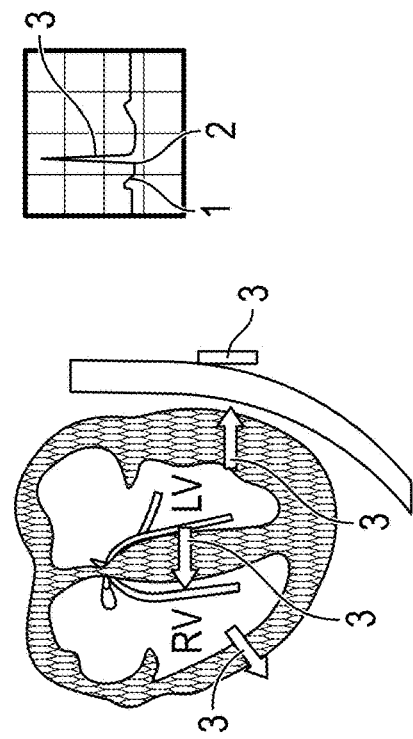

Unless otherwise noted, technical terms are used according to conventional usage. In order to facilitate review of the various embodiments of the disclosure, the following explanation of terms is provided:

"Annuloplasty element" refers to a device that induces reshaping of an annulus of the heart to repair valvular insufficiency. Such devices include those that are placed in the coronary sinus and exert their action by compressive forces on the annulus, for example by expansion of a resilient annuloplasty element, or placement of the annuloplasty element under tension, as in cerclage annuloplasty.

The term "comprises" means "includes without limitation." Thus, "comprising a guiding catheter and a guide wire" means "including a guiding catheter and a guide wire," without excluding additional elements.

The term "guide wire" refers to a simple guide wire, a stiffened guide wire, or a steerable guide-wire catheter that is capable of puncturing and/or penetrating tissue. The guide-wire also can deliver energy to augment its ability to penetrate tissue, for example by puncturing it, delivering radiofrequency ablative energy or by delivering laser ablative energy.

These are examples of a "penetrating device," which is a device capable of penetrating heart tissue, such as the myocardium.

As used herein, the term "ligature" is meant to encompass any suitable tensioning material and is not limited to only suture material. The term "tensioning material" or "ligature" includes sutures and annuloplasty wires.

A "mitral valve cerclage annuloplasty" refers to an annuloplasty procedure in which a tensioning element is placed through at least a portion (and preferably all) of the coronary sinus so that the circumferential tension is delivered around the mitral valve annulus and so that a tensioning element can be placed under selective degrees of tension to perform the annuloplasty. However, the mitral valve cerclage annuloplasty technique also includes other cerclage trajectories, such as those disclosed herein, including a trajectory through a proximal coronary septal perforator vein and myocardium or annulus fibrosis interposing between that vein and the right ventricle or right atrium to create circumferential cerclage annuloplasty tension.

"Tensioning material" is any material suitable to perform a coronary sinus mitral valve cerclage annuloplasty, in which an encircling material is placed under tension to remodel the mitral valve annulus. Examples of suitable tensioning materials are preferably a sheath material (e.g., made from a woven polymeric material) as described herein.

Unless otherwise explained, all technical and scientific terms used herein have the same meaning as commonly understood by one of ordinary skill in the art to which this disclosure belongs. The singular terms "a", "an", and "the"

include plural referents unless context clearly indicates otherwise. The term "or" refers to a single element of stated alternative elements or a combination of two or more elements, unless context clearly indicates otherwise. For example, the phrase "rtMRI or echocardiography" refers to real-time MRI (rtMRI), echoradiography, or both rtMRI and echocardiography. Although methods and materials similar or equivalent to those described herein can be used in the practice or testing of the present disclosure, suitable methods and materials are described below. In case of conflict, the present specification, including terms, will control. In addition, the materials, methods, and examples are illustrative only and not intended to be limiting.

Coronary sinus mitral valve cerclage annuloplasty is an example of a percutaneous mitral valve repair procedure for which the disclosed protective device can be used. Although the device and methods of its use are broadly applicable to any prosthetic annuloplasty element placed in the coronary sinus, the methods will be described in connection with the particular example of cerclage annuloplasty. This specific example should not be construed to limit the procedure to use with cerclage annuloplasty, but only to illustrate its use in a particular embodiment.

An exemplary transcatheter-mitral-valve-cerclage annuloplasty involves the introduction of a tensioning material or device around the mitral valve annulus using a guiding catheter and a secondary catheter, such as a steerable microcatheter directing coaxial guide wires or canalization catheter. Access to the area around the mitral-valve annulus can be accomplished using a variety of percutaneous approaches, including access from and through the coronary sinus. In particular embodiments, a tensioning material that constitutes a portion of an implant is applied around the mitral-valve annulus along a pathway that, in certain embodiments, includes an extra-anatomic portion. For example (and without limitation), the tensioning material can traverse a region between the anterobasal-most portion of the coronary sinus and the coronary-sinus ostium. As another non-limiting example, such tensioning material can be applied across the atrial aspect of the mitral valve from the posterolateral aspect to the anterior aspect of the coronary sinus, or from the septal aspect to the lateral aspect of the mitral-valve annulus. This procedure reduces the mitral annular cross-sectional area and septal-lateral wall separation, thereby restoring a line of coaptation of the mitral valve.

Figure 2:
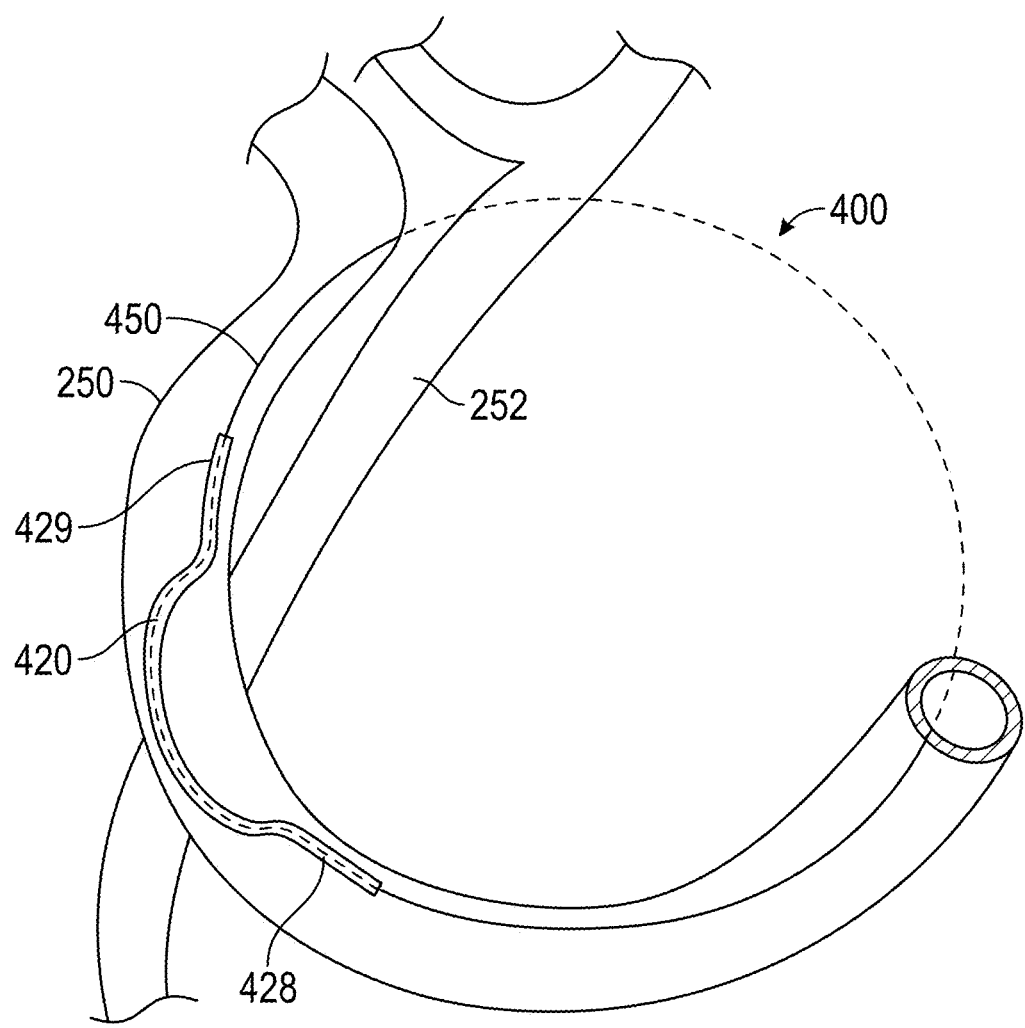
FIG. 2 is a schematic view showing an exemplary coronary protective device in position during a cerclage annuloplasty procedure.

Because it has been found that mitral annuloplasty via the coronary sinus unintentionally transmits pressure sufficient to constrict or occlude the underlying coronary artery, for illustrative purposes, some of the devices disclosed herein have been developed to increase the safety and efficacy of the procedure. FIG. 2 schematically illustrates the use of an implant 400 using a protection device 420 in a mitral valve cerclage annuloplasty procedure. FIG. 2 depicts sheath material 450 used as a tensioning element (in a preferred embodiment, braided suture material) extending through a portion of the coronary sinus 250 over a circumflex coronary artery 252. FIG. 2 shows implant 400 positioned within coronary sinus 250 with protection element 420 extending over coronary artery 252, and proximal and distal portions 428, 429 being located on either side of coronary artery 252. As tension is placed on the tether portion 450 of implant 400, the proximal and distal portions 428, 429 are held in place on either side of coronary artery 252 and transmit compressive forces to the wall of coronary sinus 250 instead of on to underlying coronary artery (LCx) 252.

Figure 3A:
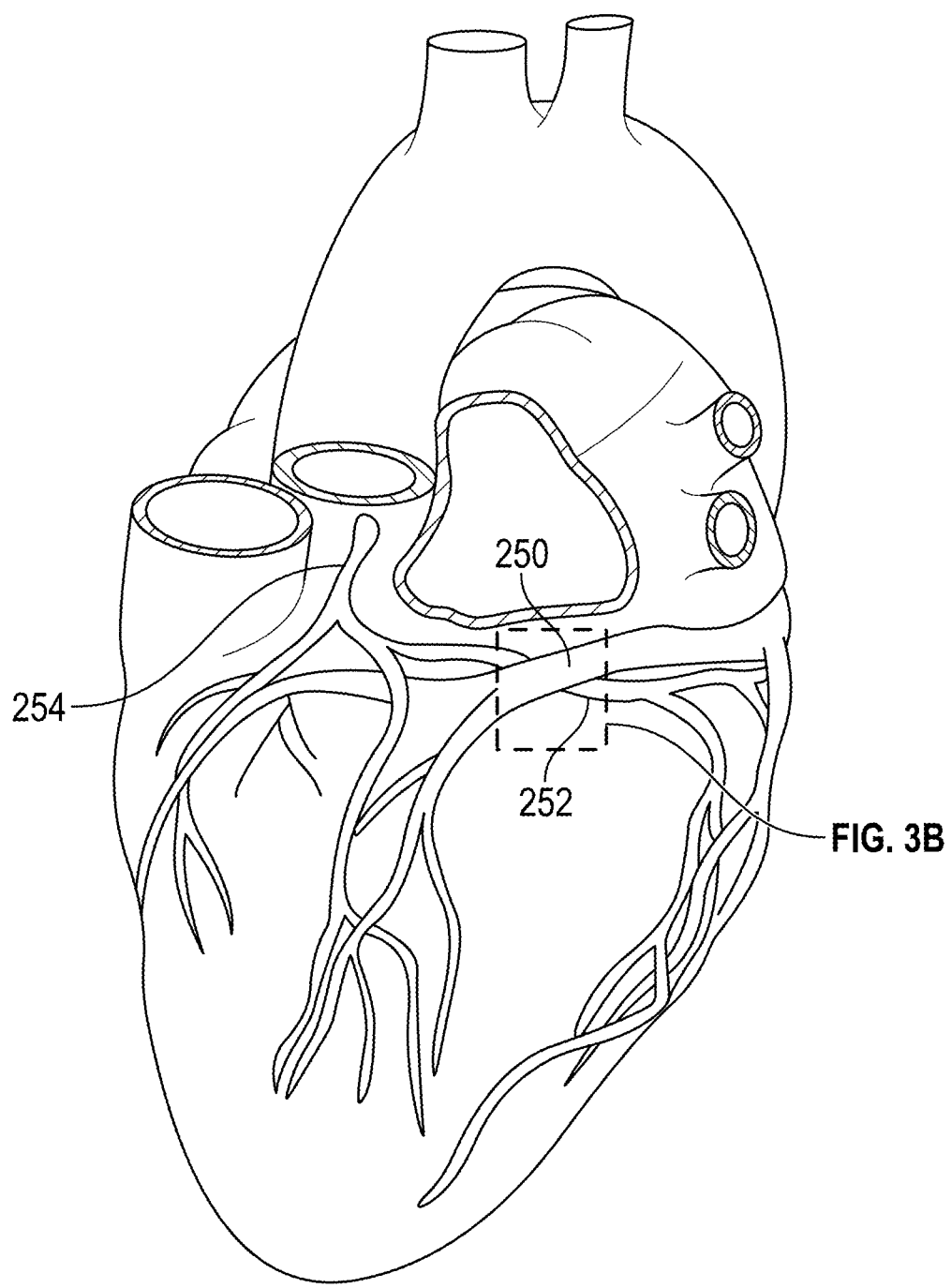
FIGS. 3A-3D is a set of drawings showing the region of the heart involved in trans-sinus coronary annuloplasty and illustrating the use of the protective device to prevent pinching of the coronary artery when tension is applied to a cerclage tensioning device.
Figure 3B:
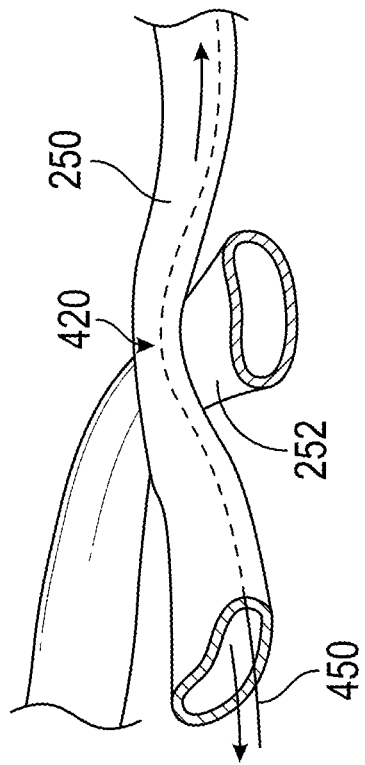
Figure 3C:
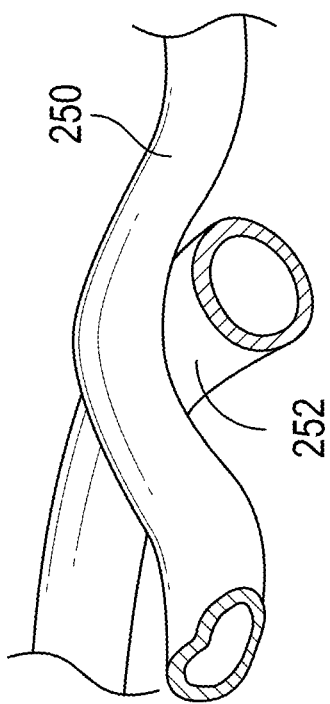
Figure 3D:
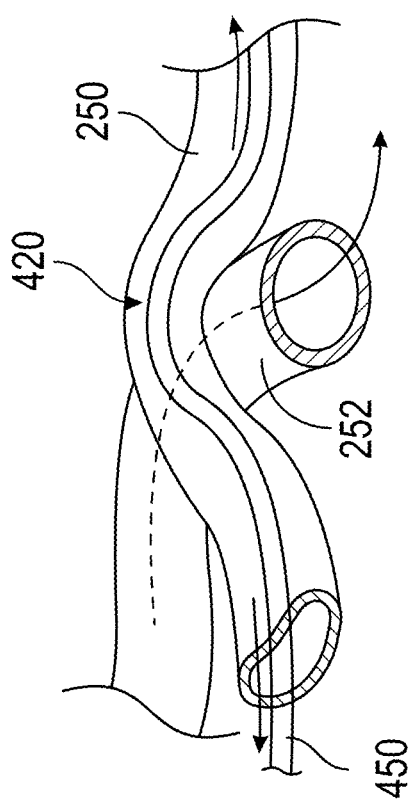

FIGS. 3A, 3B, 3C and 3D provide an alternative view of the function of cerclage annuloplasty protection device 400. FIG. 3A shows the external anatomy of the heart, with coronary sinus 250 extending over a circumflex branch 252 of a left coronary artery 254. FIG. 3B shows an enlarged view of the overlapping relationship of coronary sinus 250 to coronary artery 252. FIG. 3C illustrates hollow tether 450 placed under tension during cerclage annuloplasty which is compressing underlying coronary artery 252 and interfering with myocardial perfusion. FIG. 3D shows hollow tether 450 extending through protection device 420 which is inhibiting the application of compressive force to coronary artery 252 which therefore remains patent and able to normally perfuse myocardial tissue.

Figure 4A:
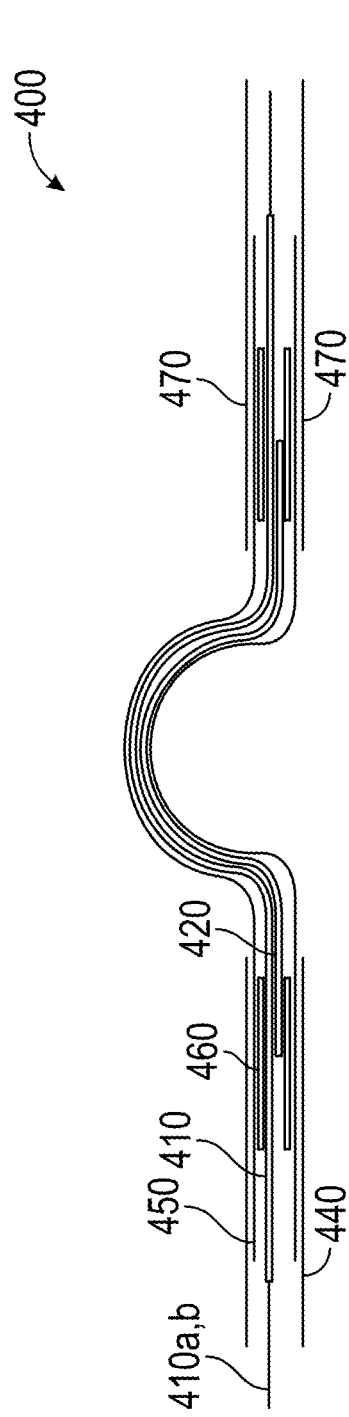
FIG. 4A is a schematic view of a portion of an implant in accordance with the present disclosure.
Figure 4B:
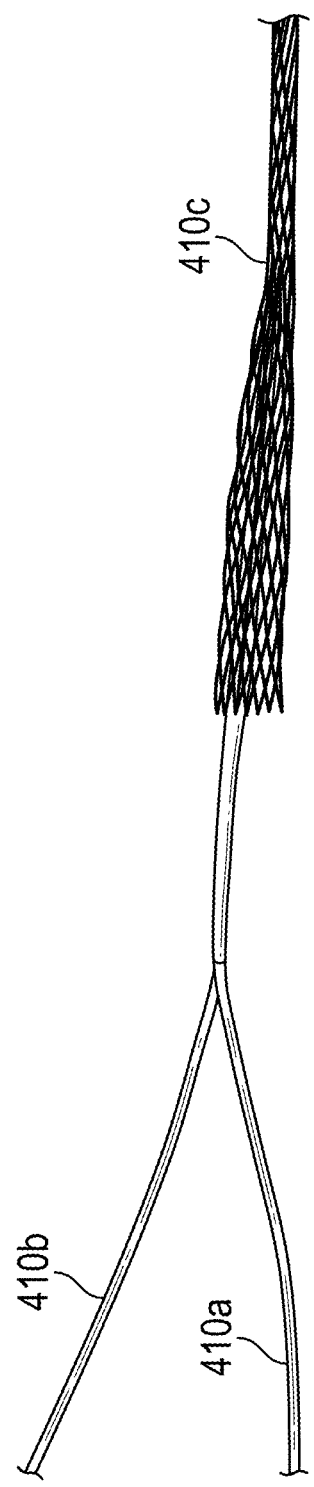
FIG. 4B is a side view of an illustrative protection element in accordance with the present disclosure.

FIGS. 4A-4B illustrate an embodiment of an implant 400 that includes a protection bridge 420. A distal end of the implant 400 is connected to a crimp 570 to facilitate its delivery as set forth below. A distal delivery tube 440 is slipped over a distal portion of a sheath 450 that houses various components of the implant 400. The crimp 570 is crimped at its proximal end around the distal end of the sheath and components inside the sheath at the distal end of the implant 400. As illustrated in FIGS. 4A-4B, the implant 400 includes an arch-shaped protection element 420. A hollow tether 410, such as a small diameter braided polyester suture, is laid on top of the protective arch 420, and secured in place, for example, by suture loops (not shown), or one or more pieces of shrink tubing (not shown). In one implementation, a piece of shrink tubing is slid over tether 410 and protective arch 420, and shrunk in place, holding tether 410 in place on the upper surface of the arch 420 from end to end. If desired, this shrink tubing can extend beyond the ends of the protection element 400 to act as a strain relief to provide a gentler transition in stiffness at the ends of the element 420. Also, if desired, additional or alternative strain reliefs 430 can also be provided at the ends of the protective element 420, also surrounding the tether 410. A sheath 450, such as a larger diameter braided suture, is then fit over the assembly of elements 410, 420, and 430, for example. Sheath 450 narrows in the regions where the protective element 420 is not present. A distal delivery tube 440 is slid over the distal region of the sheath 450, and a proximal delivery tube 470 is slid over the proximal region of the sheath 450, and if desired, crimped in place at the distal and proximal ends of the implant, respectively.

As illustrated in FIG. 4B, the inner tether 410 can be composed of a plurality of sub-components. The illustrated embodiment of inner tether 410 can be composed of an innermost metallic, radiopaque wire 410a (e.g., platinum), surrounded by a heat shrunk tubing 410b (e.g., PTFE, PET). These nested components can then accordingly be housed within braided suture 410c. Preferably, the lengths of components 410a, 410b, and 410c are coextensive with sheath 450 and crimped to sheath 450 at the proximal and distal ends of the implant 400.

Preferably, the inner tether is 410 radiopaque along its entire length to enhance visualization thereof during and after installation. While radiopacity of inner tether 410 can be enhanced by the presence of a metallic (e.g., platinum) wire, the wire, or filament, can be formed from a tungsten loaded polymer, a tantalum loaded polymer, and/or the braided suture material 410c can be used that is impregnated in one manner or another (e.g., by incorporation into the underlying polymer, or into the woven material) with one or more of bismuth, tungsten, tantalum, barium sulfate, and the like.

The delivery tubes 440, 470 are disposed over the sheath 450, and may abut, or be located near, the proximal and distal ends of the protection bridge 420. The removable delivery tubes are assembled over the continuous outer tether 450 on each side, running from the protection bridge to the exchange crimp (as illustrated in FIG. 4A) to aid in exchanging out the guide wire for the cerclage implant. Alternatively, they can be routed underneath the outer sheath 450. The removable delivery tubes can be made from polymeric material, for example, such as PEEK, HDPE, or the like, as desired. When the implant is in place, the removable delivery tubes can be removed by pulling them out. The sheath 450 surrounding the structure can, in turn, include a lubricious coating along at least a portion of its length or all of its length, such as a hydrophobic coating (e.g., PTFE, PVDF) or a hydrophilic coating (e.g., PVP). This can be provided, for example, in the form of one or more additional layers or adjacent and/or overlapping tubes of PTFE shrink tubing. The overlap regions can act as a strain relief to help provide regions of transitioning stiffness. The shrink tubing can be a multi-layer co-extrusion as described elsewhere herein that can include an intermediate braided layer formed from polymeric or metallic material, and may include radiopaque material.

In some implementations, sheath 450 can be made from a 1-2 mm ultra high molecular weight polyethylene ("UHMWPE") coreless round braid from DSM, Dyneema or Teleflex. In some embodiments, the tether/sheath 450 can be loaded with at least 20% bismuth by weight to enhance radiopacity. For example, the sheath may be loaded with between about 20 and about 70% bismuth or barium sulfate, or to any degree therebetween in increments of about 1% by weight. Additionally or alternatively, additional or alternative radiopaque materials can be incorporated into the sheath material, such as tungsten, tantalum, and barium sulfate. These materials can be incorporated, for example, as drawn metallic (e.g., platinum, or other radiopaque material) wires incorporated into the braiding, such as by weaving, or by directing the drawn wire along a central channel defined within the tether.

Figure 4D:
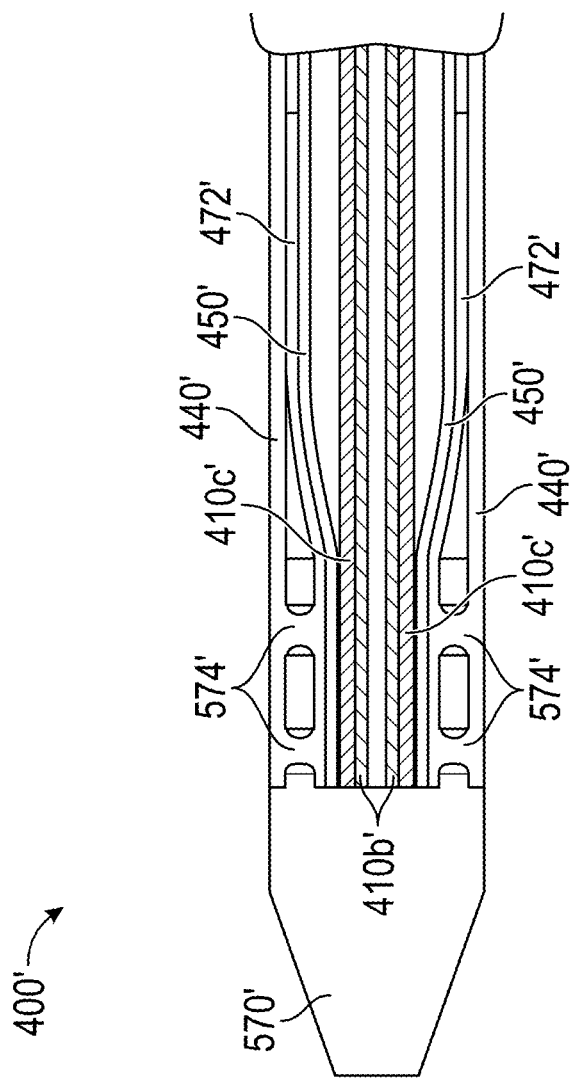
FIG. 4D is a view of an inner tether suitable for use in the implant of FIG. 4C.

FIGS. 4C and 4D illustrate a further embodiment of an implant 400' in accordance with the present disclosure. FIG. 4C illustrates a distal and central portion of implant 400'. Implant 400' includes an innermost core wire (e.g., of platinum) 410a' that is preferably housed within an elongate Pebax tube 410b'. The assembly of components 410a', 410b' are then introduced into a tubular (e.g., 0.5 mm) braided suture 410c'. This collection of components is then introduced into a shorter tube 480', preferably also of Pebax or other suitable thermoplastic material. Tube 480' is preferably only several inches long and sufficient to span the full length of protective bridge 420'. Components 410a', 410b', 410c' and 480' are then heat shrunk in a heating operation. The heating operation causes the Pebax material to melt in between the fibers of the braided suture 410', enhancing its stiffness in the region of the protective bridge 420'. The heat fused assembly of components 410a', 410b', 410c' and 480' are then laid over the upper surface of bridge 420', and then introduced into a further (e.g., 1 mm diameter) braided polymeric suture 450'. The suture 450 holds the assembly of components 410a', 410b', 410c' and 480' in place on the upper surface of bridge 420'. Next, an outer tubular layer 490' of Pebax or other suitable thermoplastic material is fitted over the portion of the outer sheath 450' that straddles the bridge 420'. This collection of components is then heat shrunk again to cause the polymeric material of components 480' and 490' to fuse into the fibers of braided sheath 450', further enhancing stiffness, and also providing a smooth surface with superior stress transition aspects along the length of the implant 400'. Inner radiopaque wire 410a' preferably does not traverse the entire length of the implant, but instead preferably occupies a central region that is between about 100 cm and 200 cm long (e.g., about 170 cm long) with roughly equal lengths on either side of bridge 420'. As further illustrated in FIG. 4D, a distal delivery tube 440' is also presented, and also preferably made from a thermoplastic polymer (preferably thermoplastic elastomer "TPE") such as Pebax. As illustrated, delivery tube 440' includes a flared proximal end suitable for abutting or even partially overlapping the distal end of bridge 420'. A proximal delivery tube 470' (not specifically illustrated) can similarly be provided with a distal flare that similarly abuts or overlaps the proximal end of the bridge 420'.

FIG. 4D shows a distal region of implant 400' showing how it is affixed to a distal crimp 570' in cross-section. Distal crimp 570' includes a distal passage for receiving a guidewire (not shown) and a proximal passage for receiving a plurality of nested tubular components. The innermost component illustrated in FIG. 4D includes Pebax tube 410b' which is nested inside braided suture 410c'. Core wire 410a' does not extend all the way to the crimp in this embodiment, although it could if desired. Component 410c' is disposed within outer sheath, or braided suture 450'. The distal end of suture 450' is in turn disposed within a short (e.g., 2-3 cm) section 572' of polymeric tube, such as Pebax. The distal end of tub 572' is fit into a cylindrical opening in the proximal face of crimp 570'. Outer delivery tube 440 is then slid over an exterior proximal portion of crimp 570', which may be recessed. Proximal portion of crimp 570' includes a plurality of holes, or windows 574', formed therethrough. Once the components are assembled, the assembly is heat shrunk to cause the polymers in the distal tip of delivery tube 440' to fuse with tube 572' through windows 574', thereby affixing crimp 570' to implant 400'. The distal end of tube 440' may initially be outwardly flared to help with initially fitting the components into or onto crimp 570'. While not shown, the proximal end of the implant 400' can be constructed similarly and fused without a crimp, for example, by heat shrinking the proximal end of the proximal delivery tube 470' to the interior components.

The disclosure also provides a version of implant 400' that does not include a protective bridge. The construction this embodiment is the same as implant 400', except that in the central region where the bridge 420' would otherwise be, the bridge 420' is not present, and tube 480' is not included. Instead, the assembly of components 410a', 410b' and 410c' are heat fused, and introduced into outer sheath 450'. In order to indicate the location of the center of the implant 400', a marker band is slid to that location over sheath 450' and held in place by sliding another polymeric tube, preferably of Pebax, over the marker, and heat shrinking it into place. If desired, a further piece of heat shrink tubing can be shrunk over the marker that may also be at least partly radiopaque to both enhance radiopacity but also to increase the thickness at the center of the implant to prevent it from being pulled through the lock as a safety feature during implantation.

FIGS. 5A-5E depict various views of a crimp 570 that provides a transition region from a proximal end 502 of a guidewire to a distal end of the implant 400. A second crimp at the proximal end of the implant 400, if provided, can provide an alternative or additional structural attachment location for affixing the proximal end of the sheath 450 to a proximal end of the inner tether 410. As illustrated, the crimp 570 includes an external proximal tapering generally conical surface, an external distal tapering generally conical surface and two intermediate tapering external conical surfaces. The distal end of the crimp is smaller in diameter than the proximal end of the crimp 570 to define a relatively large proximal bore for receiving the distal end of the implant 400 housed within and including distal end of sheath 450, and a relatively narrow, intersecting distal bore that is sized to receive the proximal end 502 of a guidewire. The crimp 570 is preferably made from a deformable metallic material that is initially affixed to the distal end of the implant 400. Once the guidewire is introduced and has been properly routed through the heart and out of the body (discussed in further detail below), the crimp 570 of implant 400 is then crimped onto the guidewire (e.g., with a hand crimper), and the implant 400, including the proximal and distal delivery tubes, protection element 420 and sheath 450 are advanced through the vasculature until the protection element straddles the LCx artery. It will be appreciated that the protection element 420 can be omitted from the implant, and, for example, replaced with a relatively straight structural element (or no stiff element at all) for patients having anatomy that does not require the arched protection element.

Regurgitation (leakage) of the mitral valve or tricuspid valve can result from many different causes, such as ischemic heart disease, myocardial infarction, acquired or inherited cardiomyopathy, congenital defect, traumatic injury, infectious disease, and various forms of heart disease. Primary heart muscle disease can cause valvular regurgitation through dilation, resulting in expansion of the valvular annulus leading to malcoaptation of the valve leaflets through overstretching, degeneration, or rupture of the papillary muscle apparatus, or through dysfunction or malpositioning of the papillary muscles. This regurgitation can cause heart rhythm abnormalities such as atrial fibrillation, which itself can cause inexorable deterioration in heart muscle function. Such deterioration can be associated with functional impairment, congestive heart failure and significant pain, suffering, lessening of the quality of life, or even premature death.

A less dangerous, minimally invasive procedure, such as percutaneous annuloplasty, permits more patients to undergo mechanical treatment of valvular regurgitation. Because the risks and complications of surgery are reduced (compared with open-heart surgery), catheter-based heart-valve procedures are suitable for a broader population of patients. Disclosed herein are improved devices and methods for catheter-based valve repair that can be used to repair damaged or malfunctioning cardiac valves, for instance, by re-apposing valve leaflets by percutaneous-cerclage annuloplasty (reconstruction or augmentation of the ring or annulus of a defective cardiac valve).

In general, the system used to carry out an annuloplasty procedure can include a guiding catheter (GC), such as a preformed transjugular balloon-tipped guiding catheter which is introduced into the coronary (venous) sinus. A retrograde coronary radiocontrast venogram pressurizes and visualizes the great cardiac vein and septal perforator veins. A high performance guidewire designed for coronary artery recanalization may be steered using a deflectable microcatheter, for example, into the great cardiac vein and thereafter into a basal septal perforator vein.

In general, an annuloplasty procedure also can include using an imaging system to image the internal bodily tissues, organs, structures, cavities, and spaces of the subject being treated. For example, transmitter or receiver coils can be used to facilitate active-device navigation using an imaging system, such as magnetic-resonance imaging (MRI). This imaging can generally be conducted along arbitrary or predetermined planes using various imaging methods based on X-ray technologies, X-ray fluoroscopy, MRI, electromagnetic-positron navigation, video technologies (such as endoscopy, arthroscopy, and the like), ultrasound, and other such technologies. In some embodiments, real-time MRI (rtMRI), intracardiac ultrasound, or electromagnetic guidance is employed. A particularly useful adjunct in cerclage annuloplasty is XFM, in which X-Ray is used with MRI to target myocardial structures, for example to help guide the annuloplasty wire in its trajectory through the structures of the heart. The XFM technique is disclosed, for example, in de Silva et al., Circulation 114:2342-2350 (2006). The guiding catheter enables percutaneous access into a subject's body, for example, percutaneous access to the heart, such as a chamber of the heart through an arm, neck, or leg vein. In some embodiments, the guiding catheter is designed for access to the ventricle and/or atrium of the heart. The guiding catheter permits introduction of one or more secondary catheters, including a valve-manipulation catheter or microcatheter or canalization-needle catheter, for example. The secondary catheter (or catheters) is used to treat, affect, or manipulate an organ, tissue, or structure of interest in the subject's body, such as the heart or particular structures within the heart. If the guiding catheter is used for percutaneous (or other) access to the heart, the guiding catheter permits introduction of one or more secondary catheters, such as a valve-manipulation catheter, into the heart while maintaining hemostasis. The secondary catheters may be coaxial or adjacent to each other, or may be introduced from multiple points of access outside the body.

Guiding catheters are available in different shapes to suit the appropriate component of the mitral-valve-repair procedure. For example, guiding catheter shapes can be provided to suit different coronary sinuses with different radii of curvature, to suit different coronary veins, transaortic as well as transseptal access routes, or to suit atria and ventricles of different calibers. All such shapes can be accommodated with appropriate primary, secondary, and tertiary curves. Examples of catheter configurations suitable to perform percutaneous transvascular mitral valve annuloplasty are known in the art and are described in detail in U.S. Patent Publication No. 2005/0216039, which is incorporated by reference herein in its entirety for any purpose whatsoever.

Figure 7A:
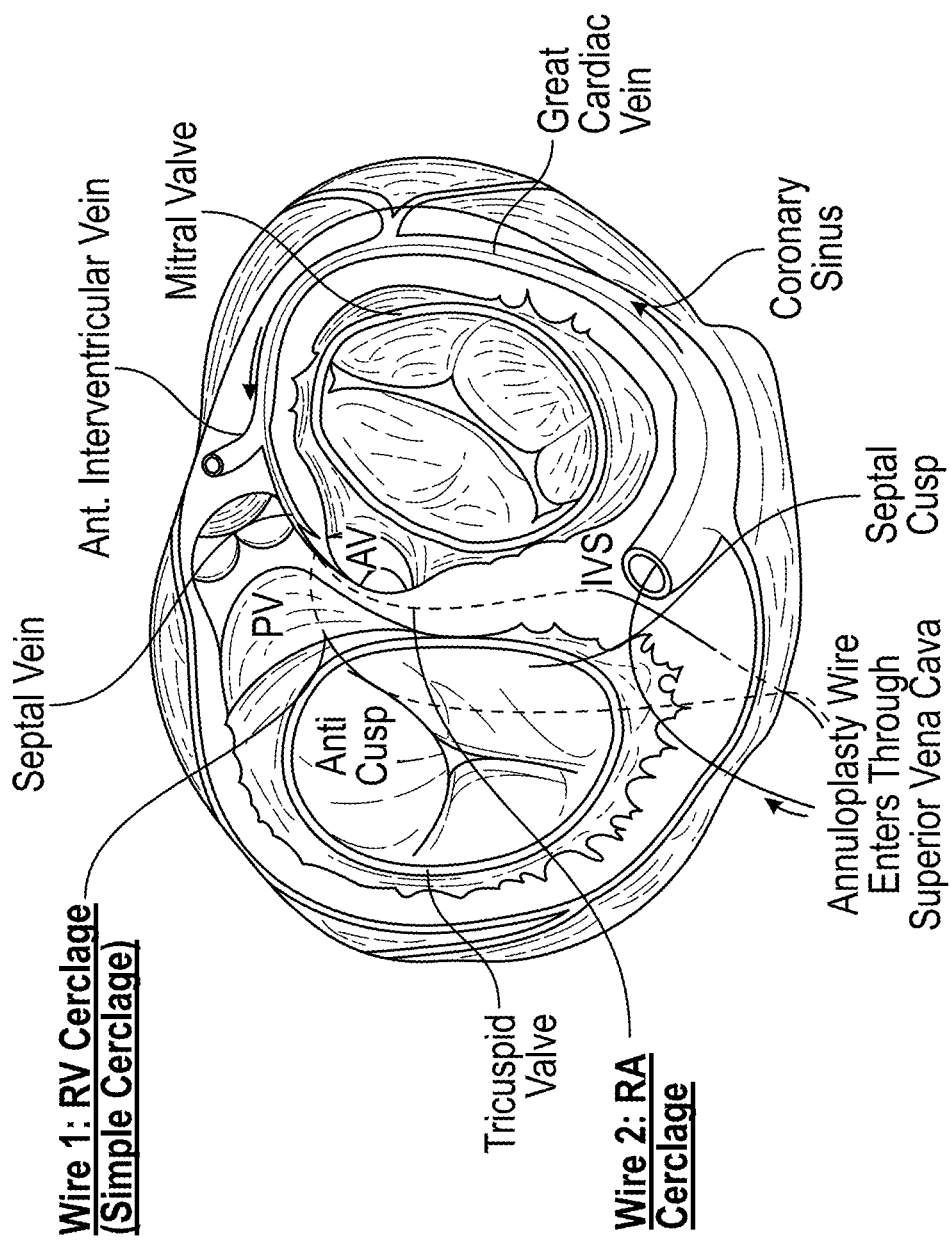
FIG. 7A is a schematic top view of a human heart, taken at the level of the atrioventricular valves, showing in dashed lines two alternative trajectories of the cerclage annuloplasty ligature around the mitral valve.
Figure 7B:
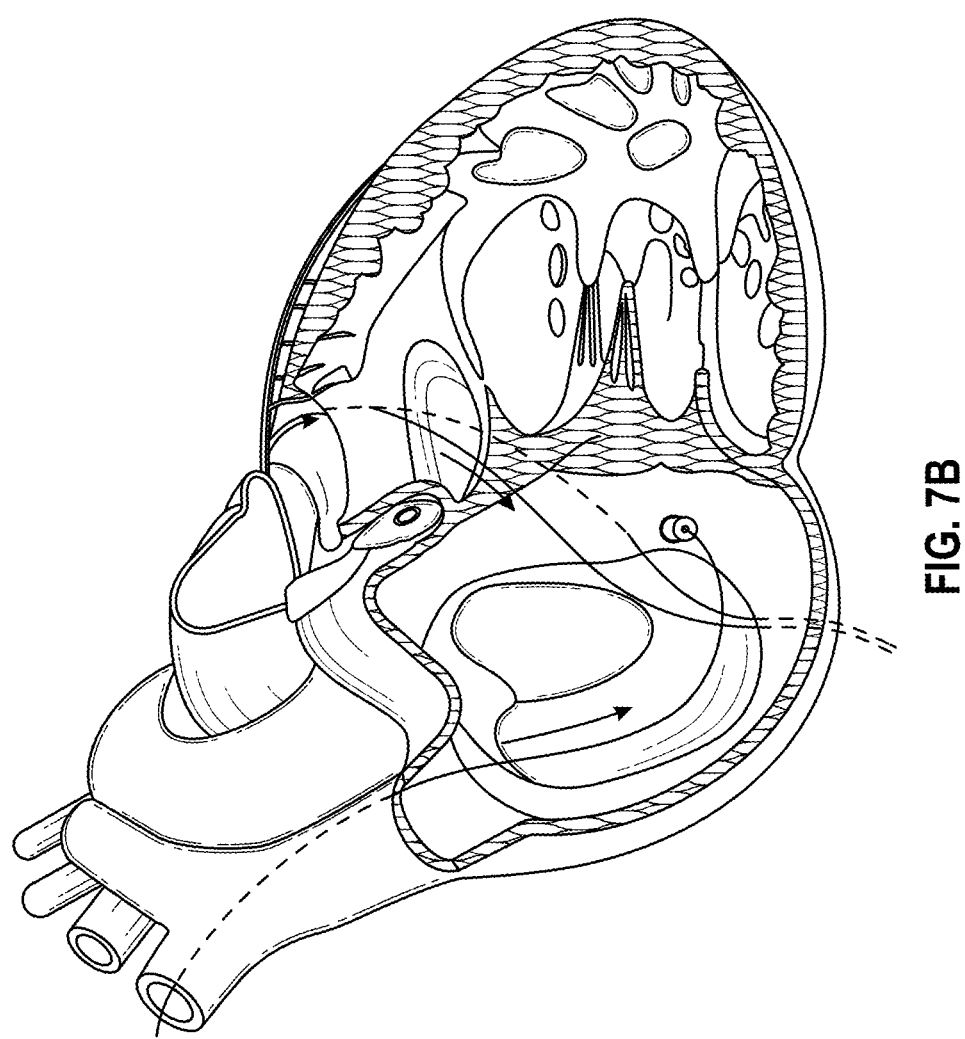
FIG. 7B is a front perspective view of the heart with portions of the myocardial wall broken away to show the cerclage annuloplasty trajectories of FIG. 7A.

Although any available approach to the coronary sinus may be used, a venous approach is preferred, for example through the jugular vein. As yet another example, the guiding catheter can be introduced into a vein, such as the femoral or jugular vein, and guided through the inferior or superior vena cava into the right ventricle of the heart. Two examples of trajectories for cerclage annuloplasty are shown in FIG. 7A and FIG. 7B. The first trajectory (labeled a "simple" or "RV" trajectory) is one in which the annuloplasty wire enters the right atrium through the superior vena cava and is then introduced through the coronary ostium into the coronary sinus. The wire is advanced through the great cardiac vein into a basal blood vessel, such as a basal septal perforator vein. The wire then exits the septal perforator vein through myocardial interstitium into the right ventricle, re-entering the right atrium along the septal tricuspid valve commissure (at the intersection of the anterior cusp and the septal cusp).

The guidewire is then retrieved using, for example, a vascular snare. Any suitable instrument can be used to capture the distal end of the guidewire and withdraw it through the vasculature until it is exposed outside the body.

An illustrative preferred and improved snare system to facilitate guidewire retrieval is also described further herein at FIG. 6.

Figure 6A:
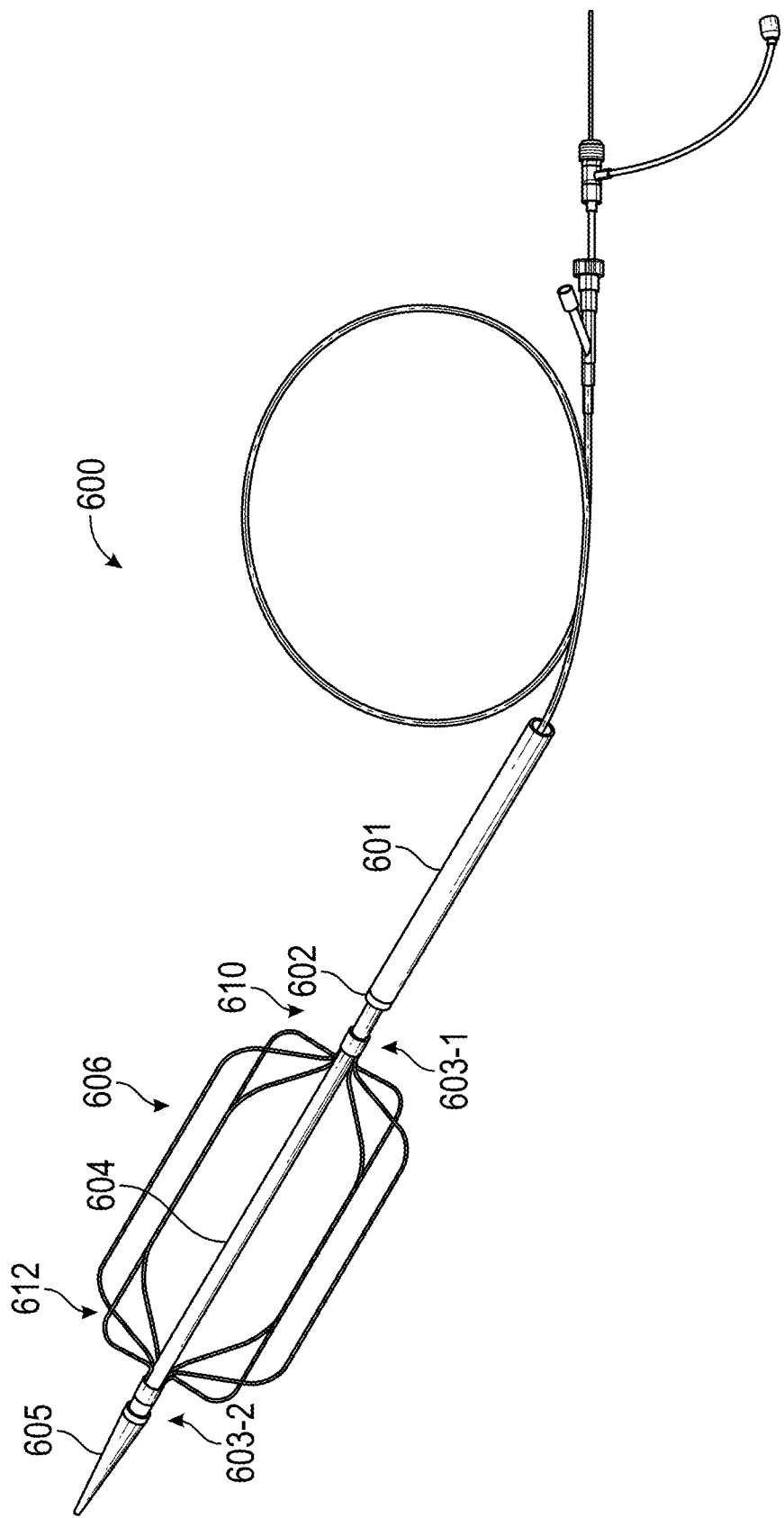
FIG. 6A is a schematic diagram of an embodiment of a snare catheter in accordance with the present disclosure.

For purposes of illustration, and not limitation, FIG. 6 illustrates an exemplary snare catheter 600 for capturing a guidewire, in accordance with the disclosure. As illustrated in FIG. 6A, the snare catheter 600 is defined by an elongate outer tubular member, or sheath, 601 that slidably receives an intermediate tubular member 602 therein along its length. The intermediate tubular member 602, in turn, includes a further elongate inner tubular member 604, such as a hypotube, slidably disposed therein along its length. Relative axial displacement of tubular members 602, 604 causes a wire snare basket 606 (e.g., a collapsible body) to expand or collapse. Snare basket 606 is defined by a plurality of pre-shaped wires, and has a proximal end 610 attached to the distal end of intermediate tubular member 602, and a distal end 612 attached to the distal end of inner tubular member 604. As such, when the ends 612, 610 are pulled away from each other by sliding tubular member 602 distally with respect to tubular member 604, the pre-shaped wires of the basket 606 are elongated and collapse radially inwardly, permitting basket 606 to then be pulled proximally with respect to outer tubular member or sheath 601. Inner tubular member 604 is preferably a metallic member, such as a stainless steel or nickel-titanium alloy hypotube that defines a further lumen along its length that can accommodate a guidewire therethrough. An atraumatic conically tapering atraumatic distal tip 605 is preferably formed over the distal end of the inner tubular member 604 and the distal end portion 612 of the snare basket 606.

After snaring the guidewire and removing the distal end thereof from the patient, the implant (e.g., 400) is exchanged for the guidewire by crimping the implant onto the proximal end of the guidewire via crimp (e.g., 570). The implant (e.g., 400) can then be advanced along the path of the guidewire as the guidewire is withdrawn from the patient until the distal end (e.g., 249) of the protection device or bridge, if provided (e.g., 420) is proximate the septum wall and the bridge is traversing the LCx artery. The location of the jeopardized coronary artery is confirmed, for example, by radiocontrast angiography. In an alternative approach, coronary veins are entered in the opposite direction from the right atrium or right ventricle under imaging guidance into a branch of the coronary sinus.

Figure 8:
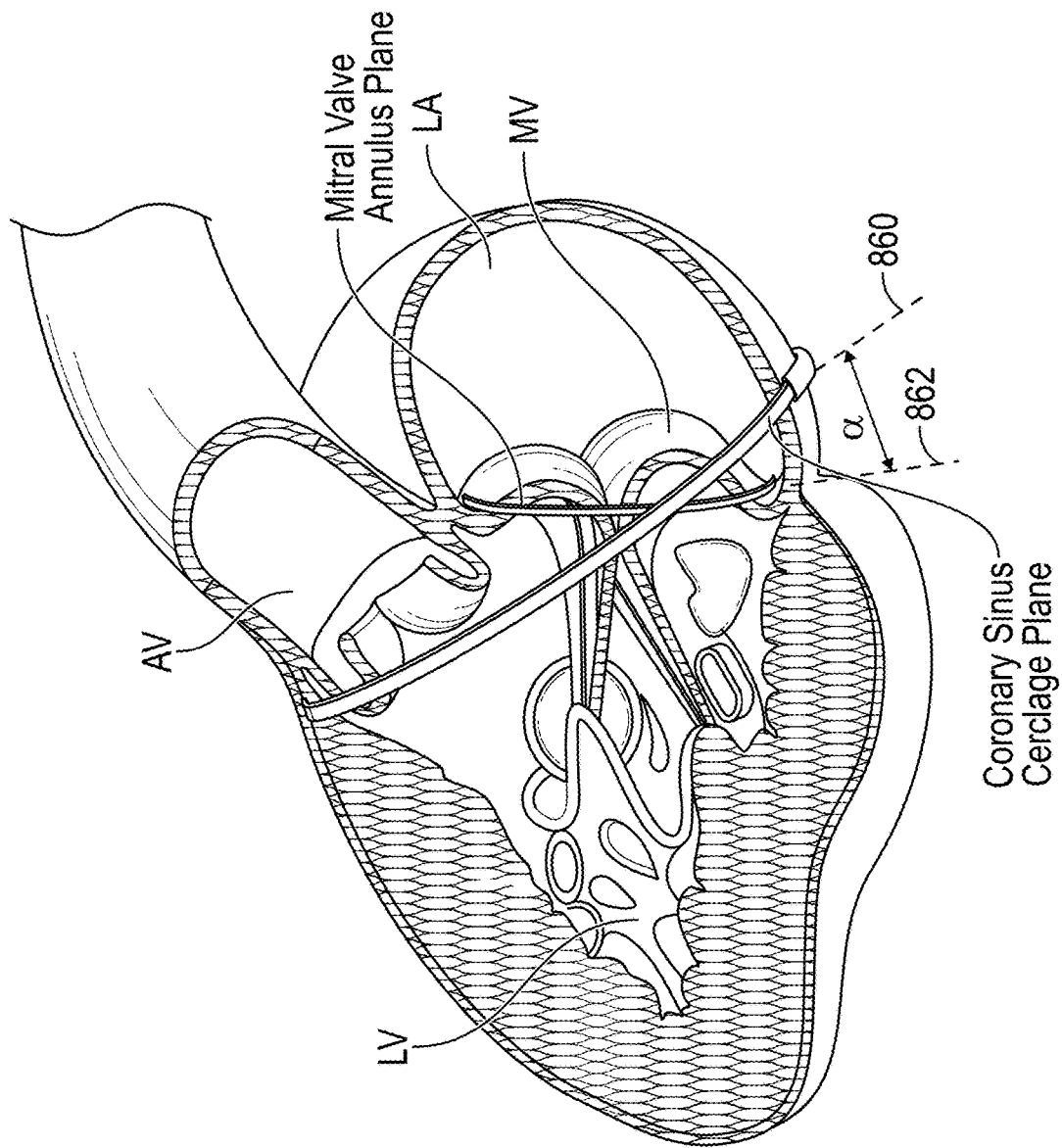
FIG. 8 is a rear perspective view of the heart showing the tilted plane of the coronary sinus cerclage annuloplasty. The drawing schematically illustrates a smaller traditional surgical mitral valve annuloplasty ring over the mitral valve annular plane and the larger coronary artery cerclage in a plane that is tilted to the mitral plane so as to encompass the left ventricular outflow tract.

An alternative or "complex" right atrial cerclage trajectory shown in FIGS. 7A and 7B extends further posterior through the basal septal myocardium into the right atrium near the coronary sinus. The wire traverses deep tissue of the septum moving in a posterior direction and exits above the opening of the coronary sinus. The plane of the resulting cerclage annuloplasty is shown in FIG. 8 to be related to and in the plane of the coronary sinus 860 such that annuloplasty remains uniquely feasible even if the coronary sinus is remote from the mitral valve annuloplasty. As the figure indicates, the plane of cerclage 860 enhances mitral valve coaptation, even when the coronary sinus is geometrically remote from the mitral valve annulus, because it is "tilted" toward the left ventricular outflow tract. The illustrated angle α between the cerclage plane 860 and the plane of the mitral valve annulus 862 is therefore advantageous. Moreover, the illustrated trajectories of the cerclage annuloplasty induces reciprocal mitral valve coaptation and left ventricular outflow tract relaxation during ventricular systole.

The guide wire is dimensioned to operate with the guiding catheter and is usually longer than the guiding catheter. For example, a guide wire of about 100 to about 250 centimeters in length and about 0.1 to about 2 mm in diameter can be used with the guiding catheter described above. If a secondary catheter, such as a tension delivery catheter, is intended for use with the guiding catheter, that secondary catheter also is dimensioned to operate with the guiding catheter and is usually longer than the guiding catheter.

The guiding catheter can be made of any suitable material or combination of materials that provide both the strength and flexibility suitable to resist collapse by external forces, such as forces imposed during bending or twisting. Exemplary materials include, but are not limited to: polymers, such as polyethylene or polyurethane; carbon fiber; ceramic; or metals, such as nitinol, platinum, titanium, tantalum, tungsten, stainless steel, copper, gold, cobalt-chromium alloy, or nickel. The guiding catheter optionally can be composed of or reinforced with fibers of metal, carbon fiber, glass, fiberglass, a rigid polymer, or other high-strength material. In particular embodiments, the guiding catheter material is compatible with MRI, for example, braided nitinol, platinum, tungsten, gold, or carbon fiber. Additionally, the exterior surfaces of the guiding catheter can be coated with a hydrophobic material or substance, such as Teflon® or other lubricous material, such as a hydrophilic material (e.g., PVP) that aids with the insertion of the guiding catheter into the body of the subject and/or aids in the movement of the guiding catheter through the subject's body.

Additionally, the guiding catheter can include a deflectable tip, such as a simple deflectable tip having a single degree of axial freedom. Exemplary (non-limiting) fixed-fulcrum and moveable-fulcrum-deflectable-tip catheters are commercially available, such as the deflectable-tip catheters described in U.S. Pat. Nos. 5,397,321; 5,487,757; 5,944,689; 5,928,191; 6,074,351; 6,198,974; and 6,346,099, each of which being incorporated by reference herein in its entirety for any purpose whatsoever. Thus, any suitable fixed-fulcrum or moveable-fulcrum deflectable-tip catheter can be adapted for use as a guiding catheter disclosed herein. The guiding catheter also can include structures or mechanisms for aiding in the rotation of the catheter about its longitudinal axis.

The guiding catheter can include a guide collar, handgrip, handle, and other structures or devices at its proximal end that aid in operation of the guiding catheter. Various control mechanisms, including electrical, optical, or mechanical control mechanisms, can be attached to the catheter via a guide collar. For example, a guide wire can be included as a mechanical control mechanism. The guide collar can include additional operational features, such as a grip for aiding manual control of the guiding catheter, markers indicating the orientation of the guiding catheter lumen or subdivided lumens, markers to gauge the depth of guiding catheter advancement, instruments to measure guiding catheter operation or physiological signs of the subject (for example, a temperature gauge or pressure monitor), or an injector control mechanism coupled to the guiding catheter lumen for delivering a small, precise volume of injectate. In some embodiments, the guide collar contains instrumentation electrically coupled to metallic braiding within the guiding catheter, thus allowing the guiding catheter to simultaneously be used as a receiver coil for MRI.

A guide wire used with the system for guiding the guiding catheter into and through a subject's body can be composed of any suitable material, or combination of materials, including the materials described above in relation to the guiding catheter. Exemplary (non-limiting) guide wires are composed of material having the strength and flexibility suitable for use with the device, such as a strand of metal (for example, surgical stainless steel, nitinol, platinum, titanium, tungsten, copper, or nickel), carbon fiber, or a polymer, such as braided nylon. Particular (non-limiting) guide wires are composed of a strand of Nitinol or other flexible, kink-resistant material. The guiding catheter or guide wire can include an image-enhancing feature, structure, material, or apparatus, such as a radiopaque marker (for example, a platinum or tantalum band around the circumference of the guide wire) adjacent its distal end. As another example, the guide wire can include etchings or notches, or be coated with a sonoreflective material to enhance images obtained via intravascular, intracardiac, transesophogeal, or other ultrasound-imaging methods. As another example, the guide wire can be coated with a T1-shortening or T2-shortening agent to facilitate passive visualization using MRI. As yet another example, a fiber-optic secondary catheter can be inserted into and through a secondary-catheter lumen of the guiding catheter to assist in visualizing the position of the guide wire within the subject as a guide wire is deployed through the distal guide-wire lumen port. In some embodiments, the guide wire and/or guiding catheter includes a structure, apparatus, or device at its distal tip useful for penetrating tissue, such as myocardial skeleton, muscle, or connective tissue. For example, the distal tip of the guide wire can be sharpened to a point for puncturing through tissue, or a secondary catheter having a coring mechanism or forceps at its distal tip can be used in conjunction with the guiding catheter. In alternative embodiments, the guide wire can deliver radiofrequency or laser ablative energy to assist with traversal of tissue. However, in alternative embodiments, the distal end of the guide wire is bent to provide a J-shaped or a pigtail-shaped tip to protect against perforation of tissue by the guide wire during manipulation. In still other alternative embodiments, the guide wire itself has a deflectable tip to facilitate traversal of tissue irrespective of natural tissue planes. One or more secondary catheters can be deployed within the lumen of the guiding catheter. Like the guiding catheter, each secondary catheter has a proximal end and a distal end; however, not all secondary catheters have a lumen. For example, non-lumen secondary catheters can include various probes, such as temperature probes, radiofrequency or cryogenic ablation probes, or solid needles.

An exemplary non-limiting secondary catheter is a canalization needle catheter, which can be deployed through the guiding catheter and into a chamber of the heart to place cerclage annuloplasty ligature through the coronary sinus around the mitral valve. A canalization-needle catheter is a type of secondary catheter that can be used to apply a suture to a bodily tissue, organ, or structure of interest.

Tension is applied via the annuloplasty cerclage through the sheath material (e.g., 450), which is preferably a hollow braided suture material as described above. Tension can be applied to both ends of the sheath (e.g., 450) as they are externalized at the point of vascular access in concert with a lock delivery catheter as described in further detail below that directs both ends of the suture through a lock mounted at the end of the lock delivery catheter. Tension in the sheath (e.g., 450) can then be secured by locking the lock of the lock delivery catheter such as that described in U.S. Pat. No. 10,433,962, for example. The lock or knot, as desired, can be located at the right atrium or right ventricle where the two cerclage trajectories cross, or at the point of vascular access, or in between the two. Tension can thus be delivered, if desired, by counterpressure against the fixation device, for example, applied through a delivery catheter. Before fixation, tension can be released or reduced, for example, to reposition the protection device or to achieve a lower degree of mitral annular circumferential reduction. As tension is applied, valvular regurgitation is preferably assessed repeatedly and non-invasively by an appropriate imaging technique. Such imaging techniques include X-ray angiography, electromagnetic position detection, MRI, external or intracavitary or intravascular ultrasound, X-ray computed tomography, pressure transducers in an affected chamber such as the left atrium or the pulmonary vein or the pulmonary artery, or a "fusion" or combination of any of the above. After the valvular regurgitation has been reduced (or even eliminated) and a desired tension is achieved, the tension is fixed using a lock or knot delivery system as mentioned above, and the excess sheath material proximal to the lock or knot can be cut and removed in any desired manner. In accordance with one aspect of the disclosure a cutting instrument can be used as described in U.S. Pat. No. 10,433,962. The use of the implant with protective device (e.g., 420) has been disclosed for use in a cerclage annuloplasty technique. However, the protective device is not needed for all patients, depending on their unique anatomy.

Figure 9:
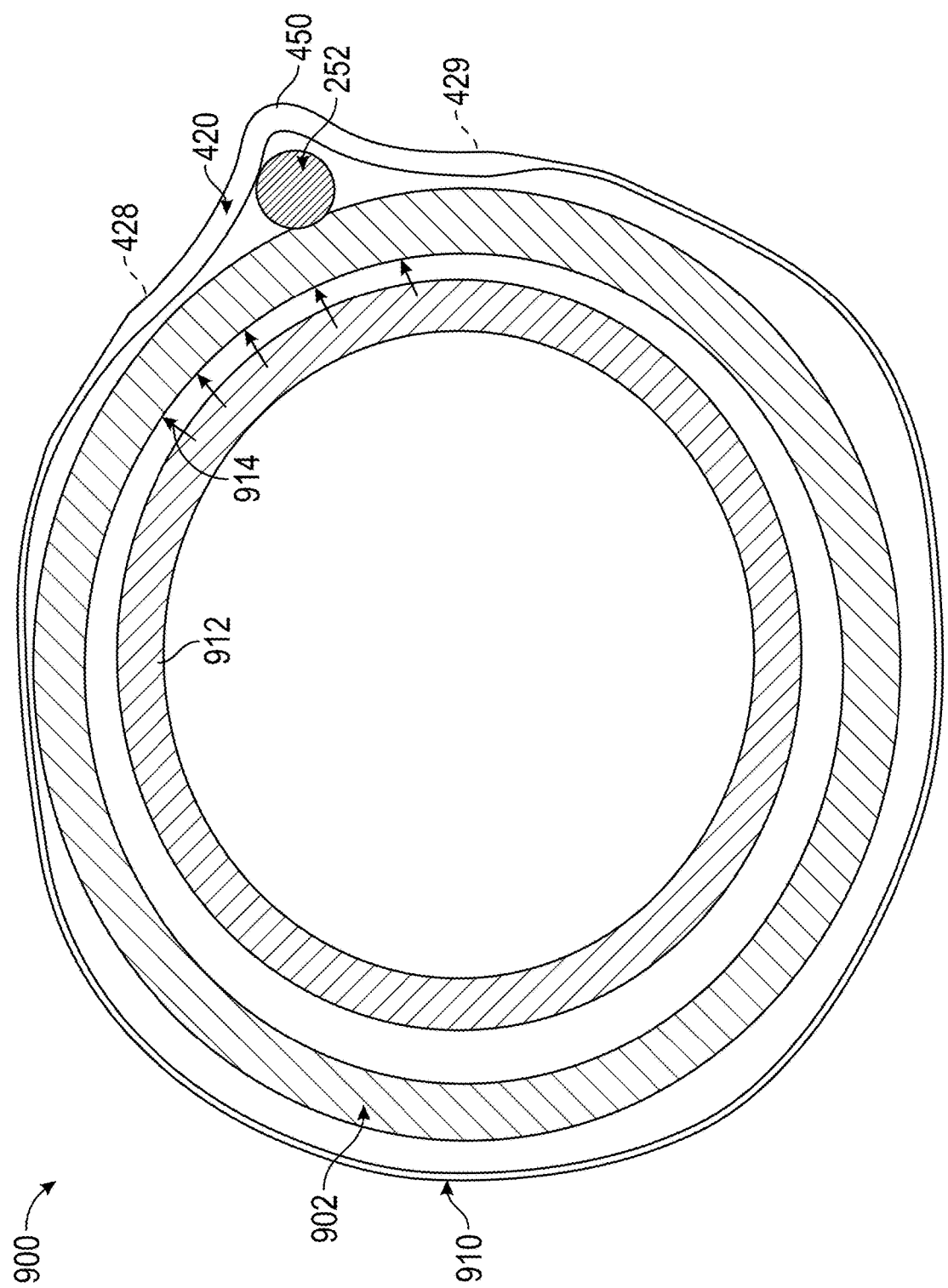
FIG. 9 is a schematic cross-sectional view of the mitral valve region of a heart wherein a prosthetic heart valve is positioned within the mitral valve region and applies an outward expansion force and a mitral cerclage implant in accordance with the disclosure is positioned around the mitral valve region and applies an inward force, and a coronary protection device in accordance with the disclosure is positioned along the mitral cerclage device to protect the coronary artery from being compressed.

FIG. 9 is a schematic cross-sectional view of the mitral valve region of a heart showing an exemplary implant system 900 that includes an implanted TMV 912 positioned within the heart wall 902 and a mitral cerclage annuloplasty device 910 positioned around the heart wall. The device 910 includes an arched protection device 420 spanning over a coronary artery 252 to protect the artery from compression applied by both the device 910 from the outside and outward expansion force 914 applied on the inside of the heart wall 902 by the TMV 912. The exemplary protection device 420 includes an arched portion extending between two flattened, generally coplanar proximal and distal segments 428, 429. The bridge, or protective device 420 can have any combination of features and dimensions described herein with regard to other exemplary protection devices.

Figure 10:
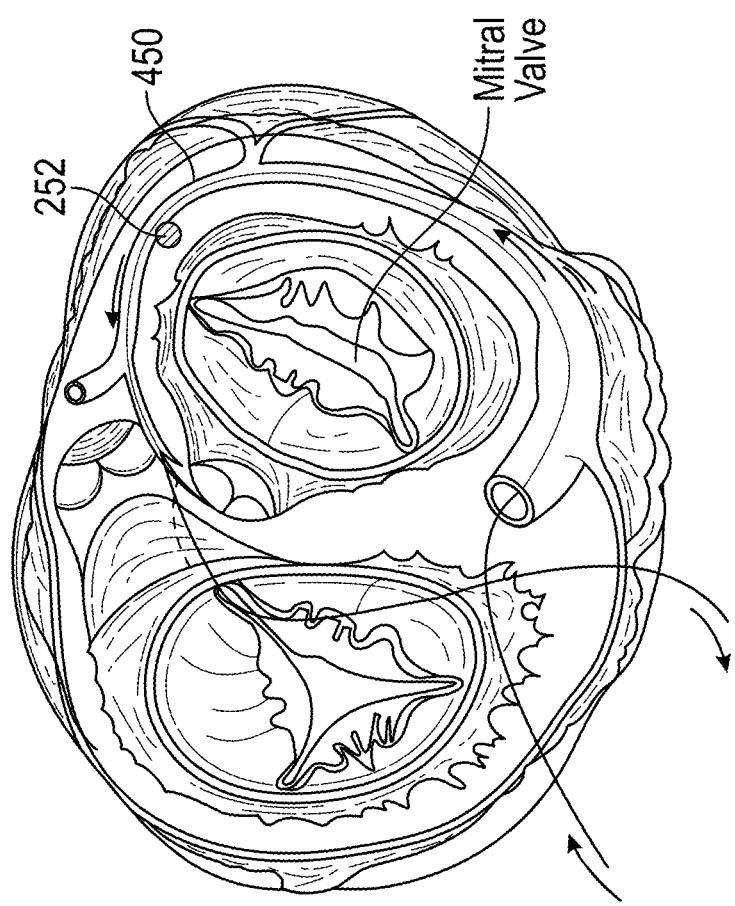
FIG. 10 is a cross-sectional view of a heart with a mitral cerclage device being delivered through the coronary sinus and around the mitral valve.

FIG. 10 shows a tensioning suture (e.g., 450) extending through the coronary sinus 250 partially around the mitral valve without the inclusion of the disclosed protection device. Consequently, the circumflex coronary artery 252 is entrapped under the tensioning suture as the coronary sinus overlaps the artery, applying unwanted compression on the artery. When a TMV is also implanted within the mitral valve, it can apply additional inside-out compression force on the artery 252. Without the protection device, the artery 252 can collapse and/or be pinched by the opposing forces.

FIGS. 11A-11E illustrate implementations of a spacer to be coupled to an implant in accordance with the disclosure to be located at least partially within a cardiac valve, such as the tricuspid valve. The spacer is preferably coupled to a cerclage implant as depicted in the present disclosure, but it is also possible to anchor the spacer in place by way of other means such as an expanding frame that resides within the vasculature of the patient, and the like.

FIG. 11A depicts aspects of a spacer 1100 in accordance with the present disclosure without a covering so as to illustrate the internal components. As illustrated, the spacer 1100 is formed from a plurality of elongate members 1106. Each elongate member 1106, or filament, can be a wire made from shape memory material such as NiTi alloy material. But it will be appreciated that other materials can be used. Each elongate member 1106 is connected to other filaments in the structure at a proximal end, or hub, 1102 and a distal end, or hub, 1104. Each hub can be formed, for example, from a crimp or tubular section to which the filaments 1106 are attached. The proximal hub 1102 is coupled to a lock or lock housing 1108 by way of a tether or cable 1110.

Figure 11E:
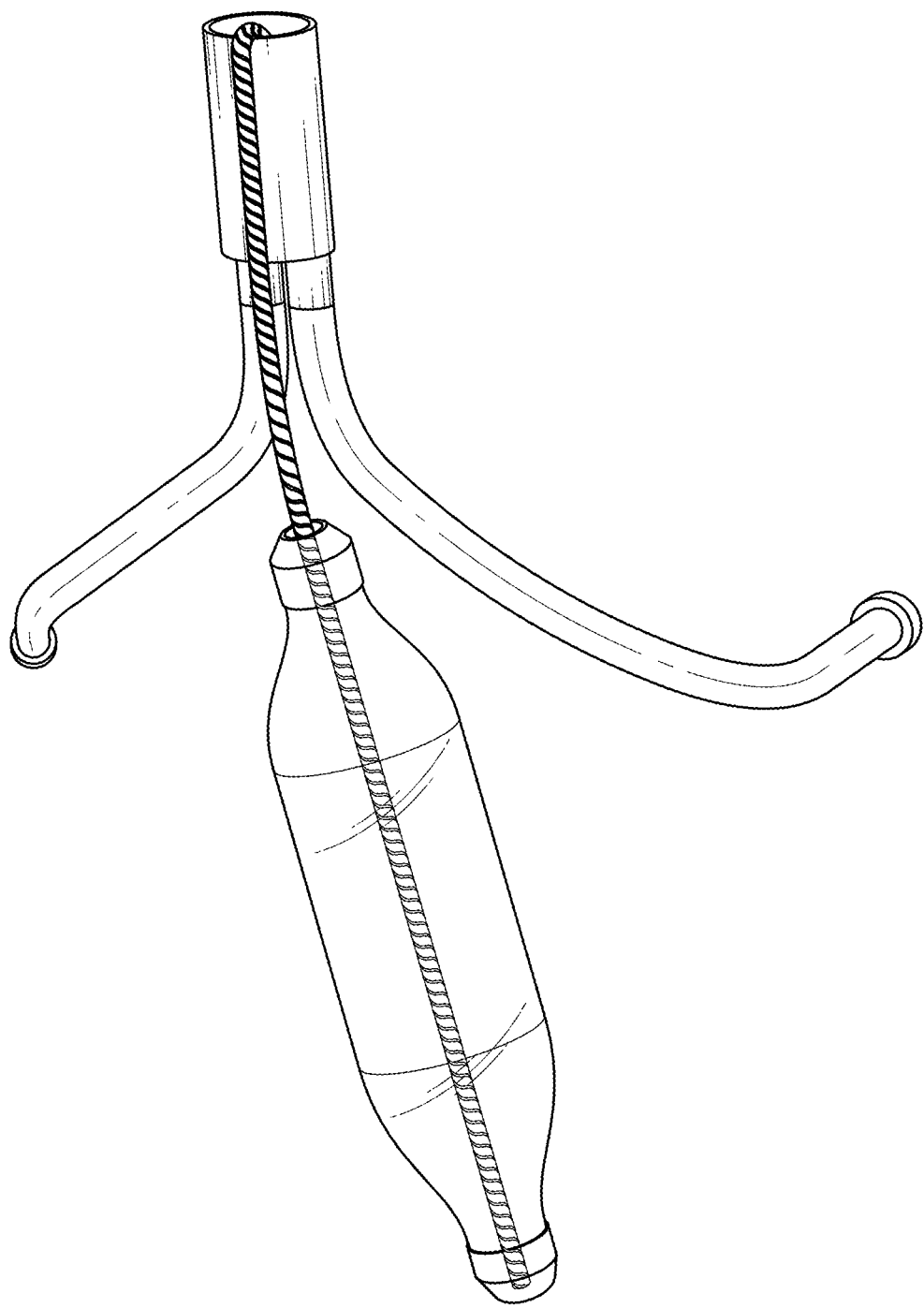

In the illustrated embodiment of FIG. 11A, is made from DFT® wire (e.g., from Fort Wayne Metals, Fort Wayne, Ind.) including a NiTi tube filled with platinum wire so as to provide a combination of shape memory characteristics from the NiTi material and radiopacity from the platinum material. The NiTi material is configured to self-expand into the depicted expanded configuration from a collapsed linear configuration wherein the filaments 1106 are all radially inwardly compressed, such as inside of a delivery catheter. When the device is deployed out of the end of a tubular catheter, it takes on the depicted shape. The tether or centering arm 1110 can also be made from NiTi material and is intended to project outwardly into the vasculature to permit the spacer to center in the lumen so it is disposed approximately in the center of the tricuspid valve, in this example, to permit the leaflets of the tricuspid valve to coapt against the surface of the spacer 1100. The lock 1108 and spacer is introduced by threading the lock 1108 carrying the spacer over the tethers formed from sheath 450 of the cerclage implant. As illustrated, the lock 1108 is configured to slide around and attach to the lock of the cerclage implant to which the tubular limbs of the cerclage implant attach. Relative orientation of the lock 1108 and lock and limbs of the cerclage implant is depicted in FIG. 11E.

FIG. 11B once again depicts the embodiment of FIG. 11A alongside the embodiments of FIG. 11C and FIG. 11D. The embodiment of FIG. 11A is preferably provided with a membrane covering that covers the filaments 1106 to enclose the volume defined by the filaments. FIG. 11C depicts a relatively large diameter balloon and FIG. 11D depicts a relatively small diameter balloon that can be used instead of the embodiment of FIG. 11B. The balloon can be configured to self-expand by way of filaments (e.g., 1106) as with the embodiment of FIG. 11B or other expanding structural elements. The balloon can similarly be filled with a fluid such as saline or the like. The specifically illustrated embodiments of FIGS. 11C and 11D include inflatable balloons that are connected at their proximal and distal ends to an elongate inner structural member or tether 1114, such as a NiTi wire that extends through the proximal end of the balloon and couples to the lock 1108. FIG. 11E depicts the embodiment of FIG. 11D disposed over the wishbone lock of a cerclage implant.

Figure 12A:
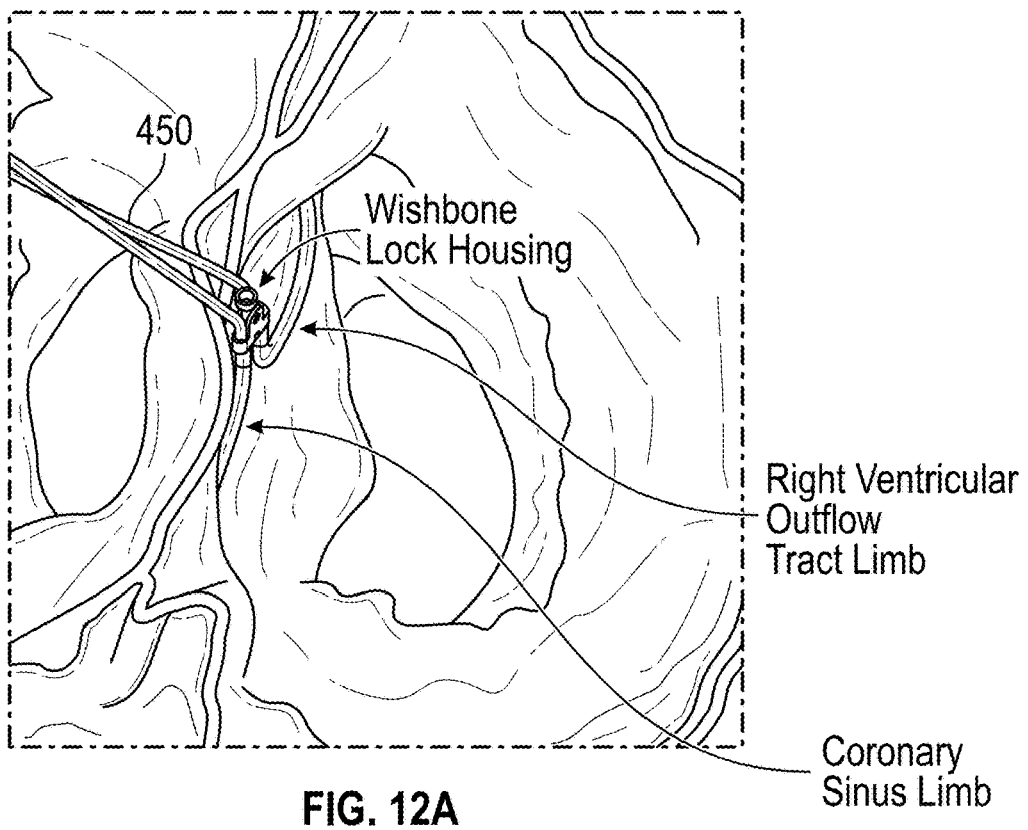
FIGS. 12A-12C illustrate placement of a first implementation of a spacer in the location of a tricuspid valve in accordance with the present disclosure.
Figure 12B:
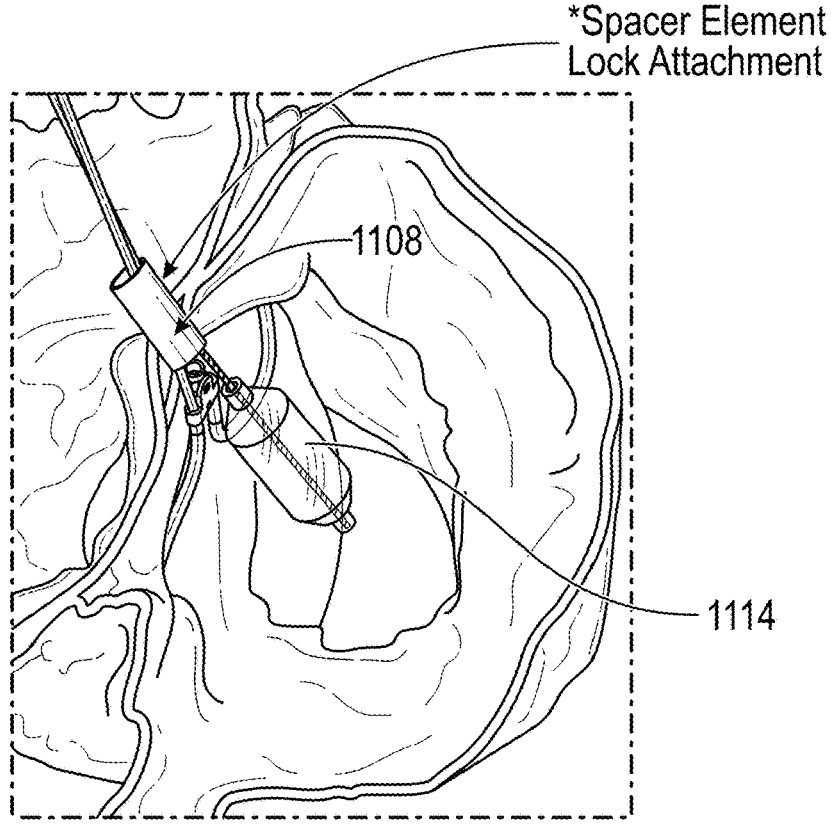
Figure 12C:
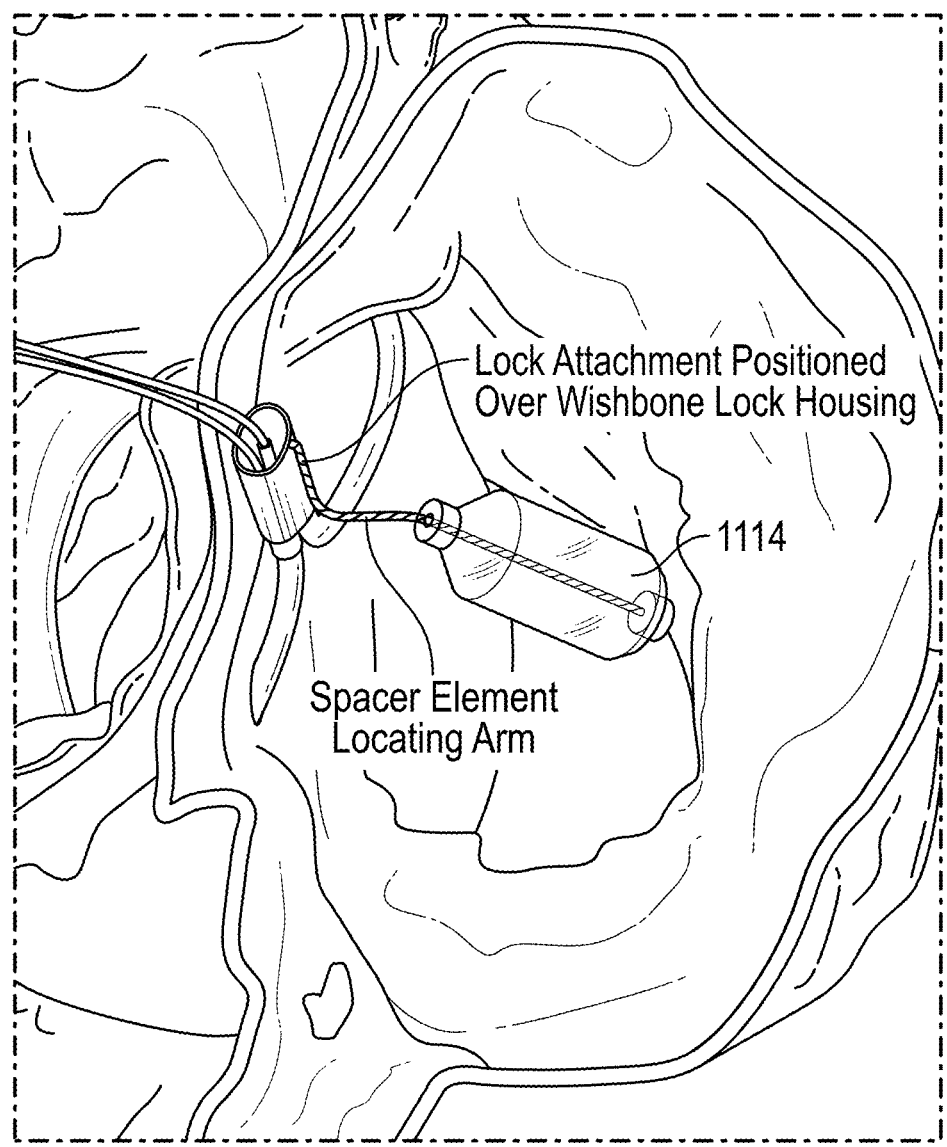
Figure 13C:
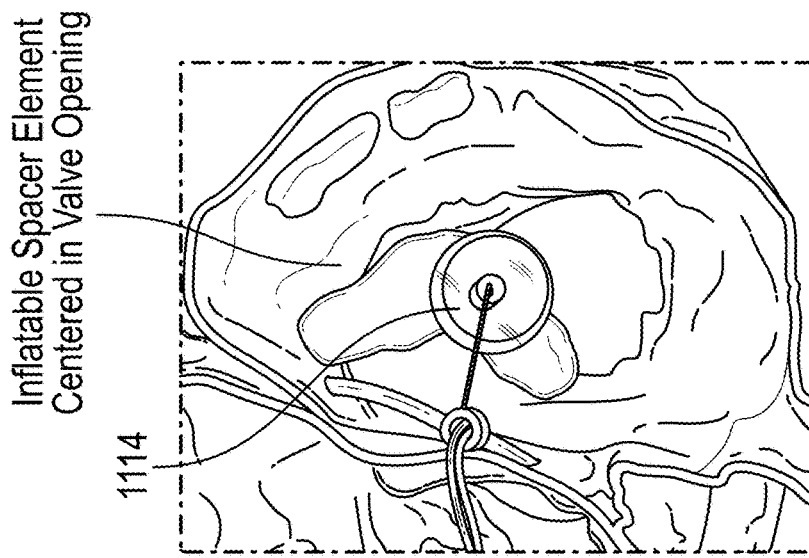
FIGS. 13A-13C illustrate placement of a second implementation of a spacer in the location of a tricuspid valve in accordance with the present disclosure.
Figure 13B:
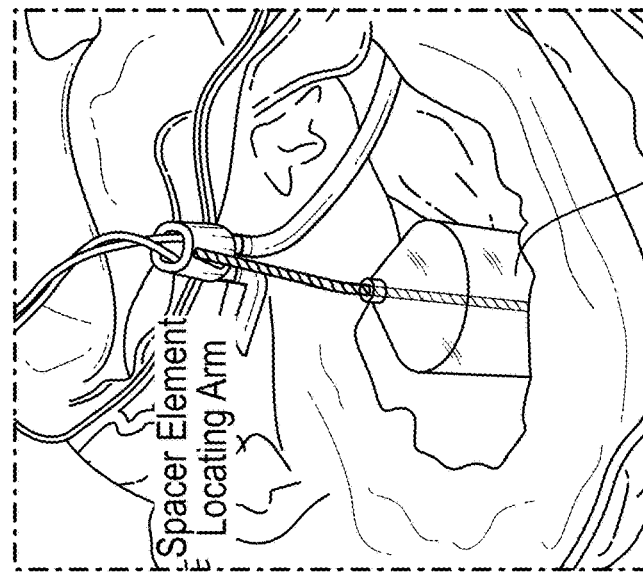
Figure 13A:
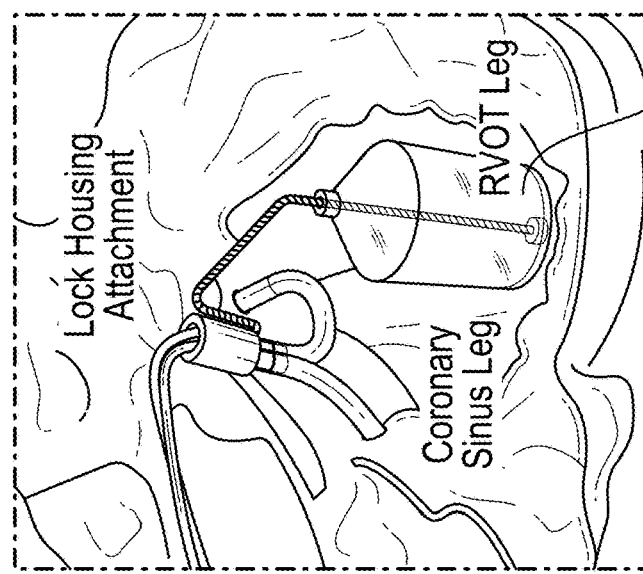

FIGS. 12A-12C illustrate placement of a first implementation of a spacer in the location of a tricuspid valve in accordance with the present disclosure. Specifically, for illustration purposes, a polymeric reproduction of a heart is used to demonstrate placement of the cerclage implant, as described elsewhere herein and in U.S. Pat. No. 10,433,962. Specifically, after the body of the implant including sheath 450 is routed through the limbs of the lock assembly, and after the lock is locked in place to place the mitral annulus under tension, the end or ends of the sheath 450 that are accessible are used as a guide rail wherein the lock 1108 is threaded over one or both ends of the sheath 450 and delivered over the lock so that the spacer 1100 protrudes into the area of the tricuspid valve. Once the desired placement is obtained, by adjusting the axial and rotational position of the lock 1108, the lock is locked in place. The lock can be locked in place by way of an interference fit, and/or it may latch onto the lock of the cerclage implant. By way of further example, the lock 1100 can be advanced over one of the two ends of the sheath 450 parallel to the other tether, and a knot may be pushed along both of the tether ends 450 down over the lock 1108 to hold the spacer implant 1100 in place in the tricuspid valve. During installation, adjustments of the spacer 1100 can be made in real time under visualization and contrast fluid to ensure that the spacer 1100 is properly placed in the tricuspid valve to ensure optimal coaptation of the valve leaflets. The spacer 1100 can be coupled to the distal end of a delivery catheter (not shown) by way of a releasable connection (e.g., threaded connection to component 1108), and the delivery catheter can be threaded along the tether or tethers 450 in an over the wire (OTW) or rapid exchange (RX) configuration. The lock 1108 can then be slid over the lock of the cerclage implant, and locked in place. FIGS. 13A-13C illustrate placement of a second implementation of a spacer in the location of a tricuspid valve in accordance with the present disclosure. FIG. 13A illustrates the inflated spacer positioned over uncut implant tethers 450. FIG. 13B illustrates relative placement of the wishbone lock structure of the cerclage implant, and the positioning of the spacer 1100 laterally, whereas FIG. 13C depicts relative placement in the tricuspid valve area from an axial perspective.

Figure 14B:
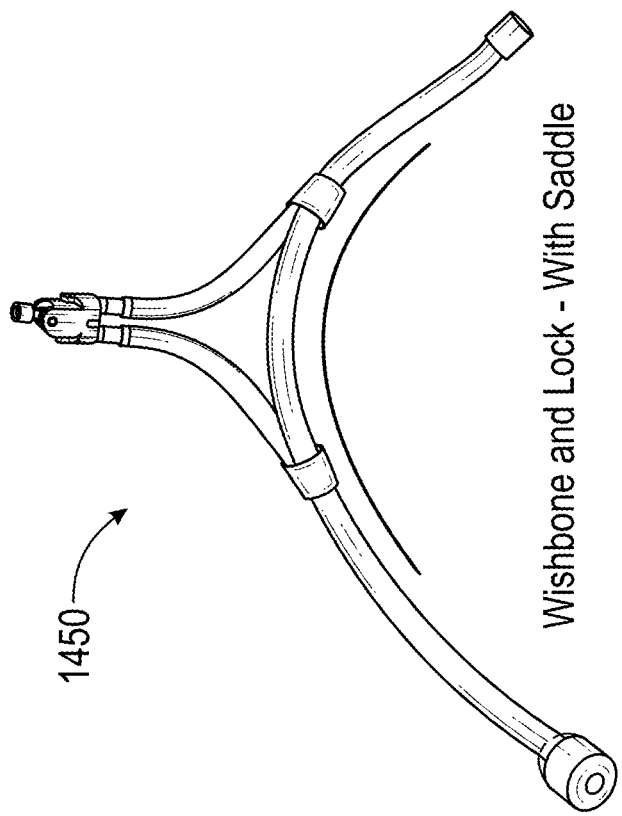
FIGS. 14A-14B illustrate aspects of embodiments of an implant in accordance with the disclosure.
Figure 14A:
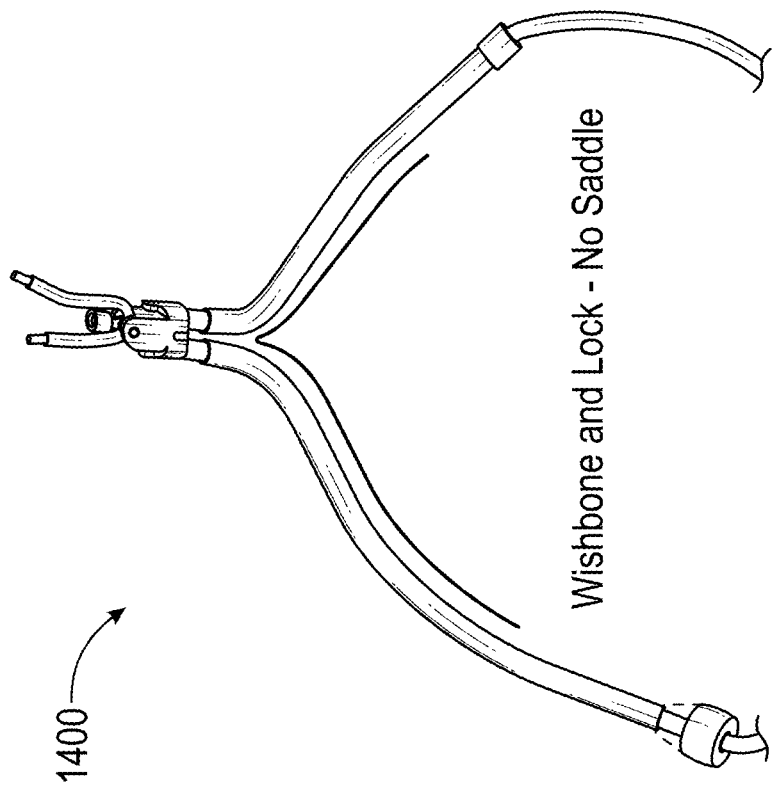
Figure 14C:
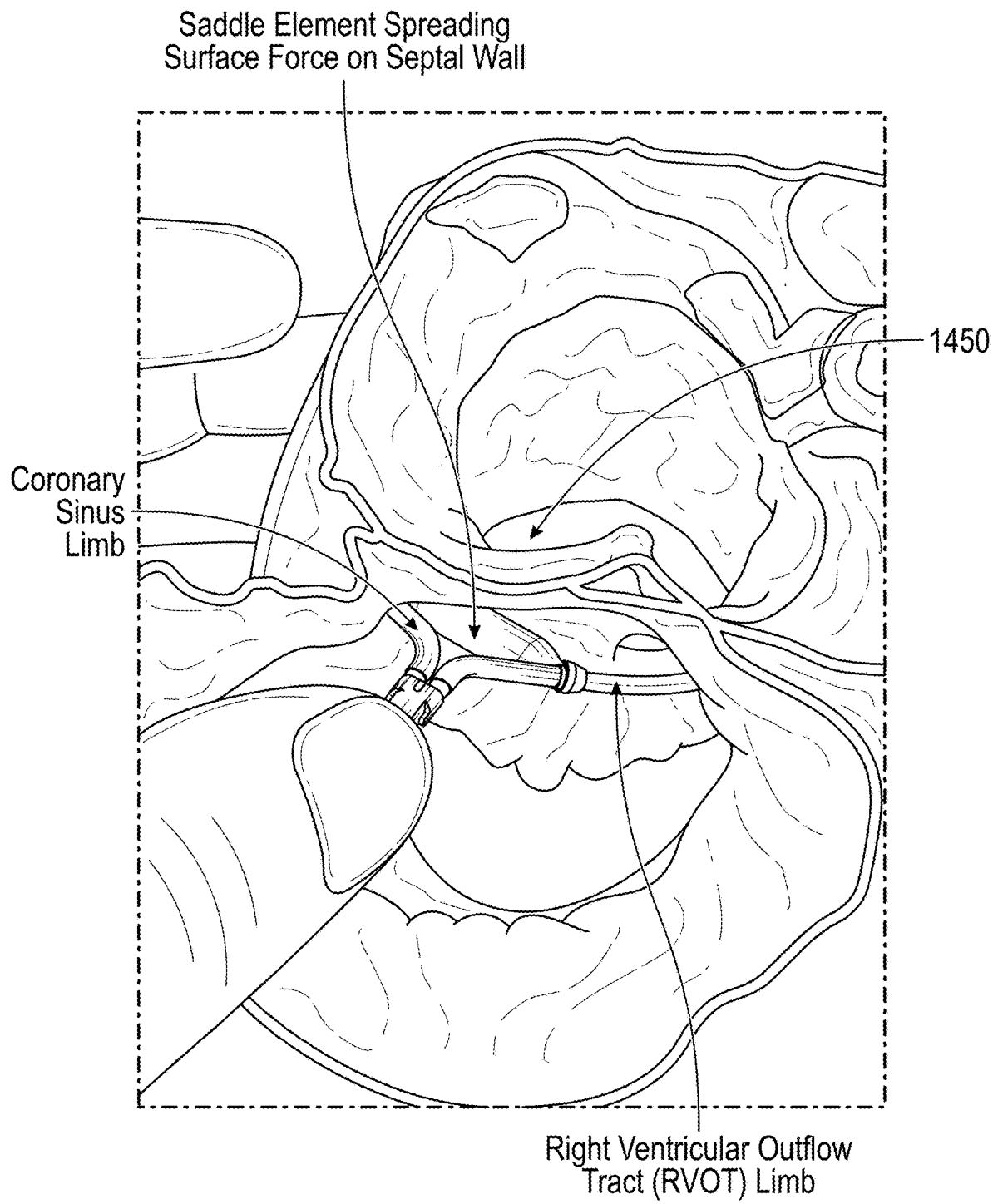
FIG. 14C illustrates implantation of the implant embodiment of FIG. 14B.

FIGS. 14A-14B illustrate aspects of embodiments of an implant in accordance with the disclosure. Specifically, FIGS. 14A-14B depict aspects of a mitral cerclage implant lock and limbs configured for jugular access. FIG. 14A depicts the jugular access cerclage wishbone and lock without a "saddle" attachment, whereas FIG. 14B depicts the implant with a "saddle" attachment. The saddle attachment is coupled at either end to each of the limbs that extend outwardly from the lock. The saddle attachment benefits operation of the lock and limbs by helping to limit separation of the limbs of the device when it is placed under the tension by way of the sheath 450. Additionally, the saddle helps to spread out mechanical stress along its length and thereby distribute stresses more evenly over the cardiac tissue as compared to not using the saddle. This also creates a more uniform surface along the coronary sinus and RVOT limbs. FIG. 14C illustrates implantation of the implant embodiment of FIG. 14B, illustrating placement of the right ventricular outflow tract (RVOT) limb through the tricuspid valve. FIG. 14C further illustrates the placement of the saddle portion along the septal wall, illustrating how it spreads stress across the surface of the septal wall.

Figure 15:
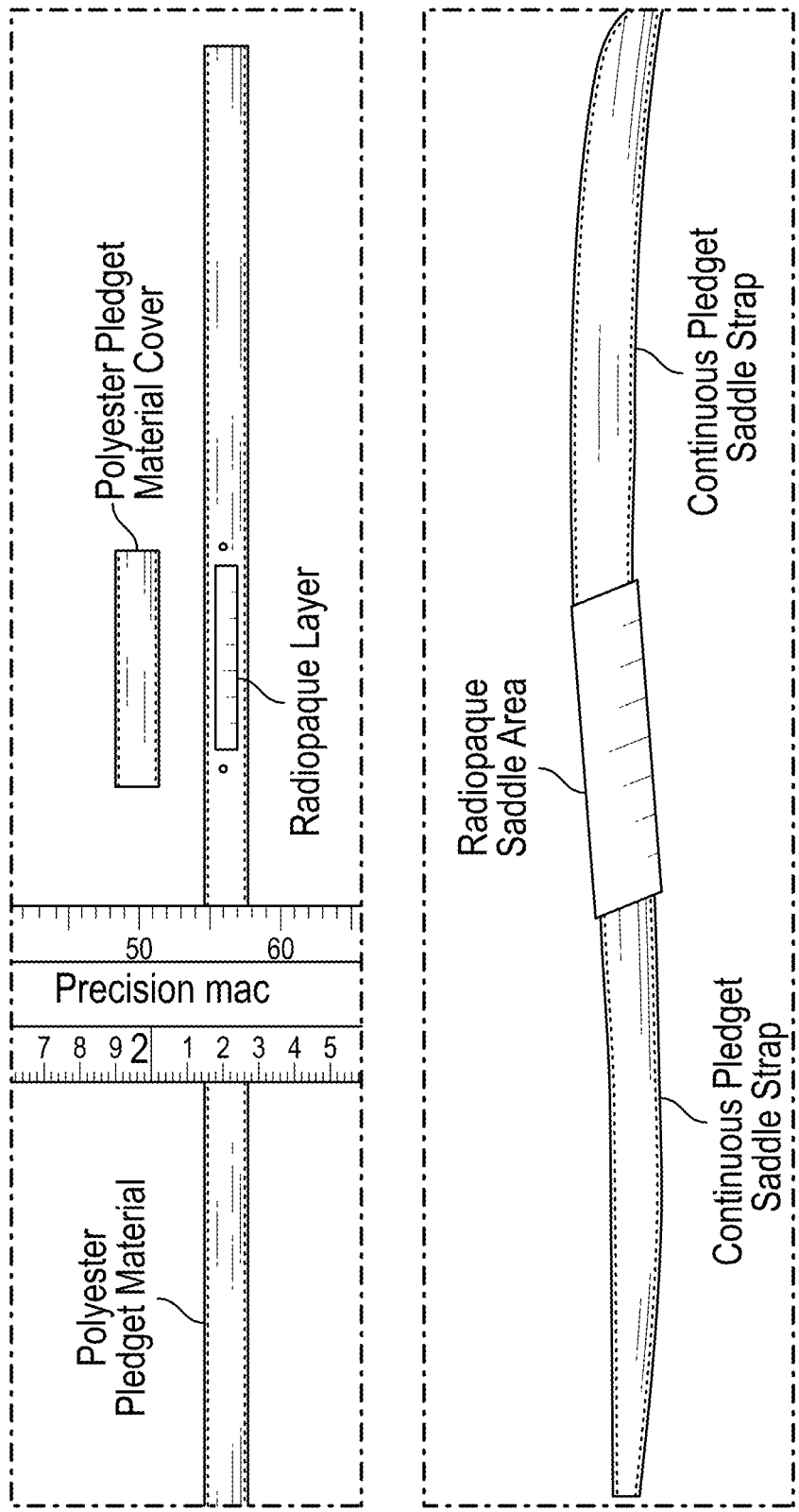
FIG. 15 illustrates aspects of construction of an implant in accordance with the disclosure.

FIG. 15 illustrates aspects of construction of a version of the saddle attachment in accordance with the present disclosure. The saddle attachment is composed of a polyester pledglet material that includes a layer of radiopaque material to assist in visualization disposed thereon. The radiopaque layer includes a polyester pledglet material cover disposed thereover to sandwich the radiopaque material within the saddle. The pledglet band is configured to be in continuous contact with the tissue. The radiopaque material can take on a variety of forms, including radiopaque polymer beading, a flat ribbon loaded with radiopaque material, a polymeric ribbon loaded with radiopaque material, radiopaque ink disposed on the pledglet material, a suture loaded with radiopaque material, metallic marker bands surrounding the saddle, and the like. In the illustrated embodiment of FIG. 15, a section of pledglet material is sewn over the radiopaque material onto the continuous pledglet strap to encapsulate it. The band that forms the saddle can then be attached to the CS and RVOT limbs of the lock in a variety of manners. For example, the saddle can be attached to the wishbone limbs by reflowing polymer over the assembly, and/or wrapping the ends of the saddle over the limbs with suture material. It will be recognized that a variety of techniques can be used to bond the saddle to the limbs and that the depicted techniques are merely illustrative.

Figure 17B:
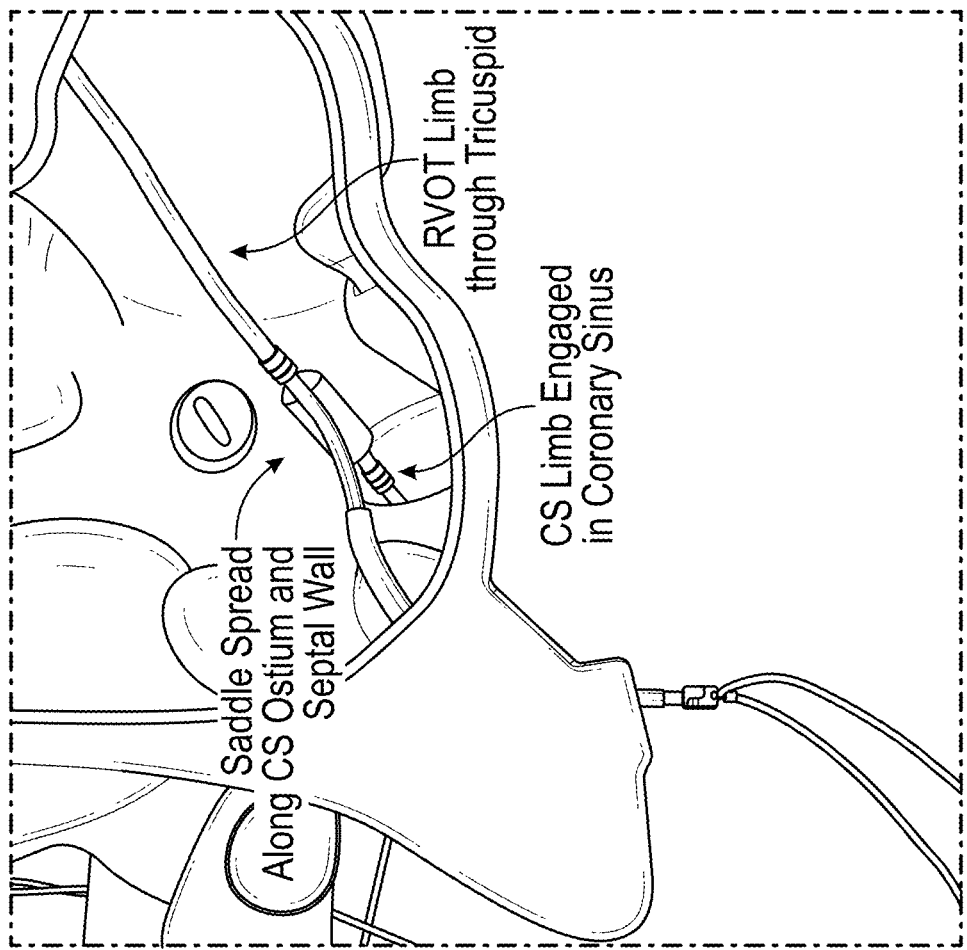
FIGS. 17A-17C illustrate views showing placement of an implant in accordance with the present disclosure.
Figure 17A:
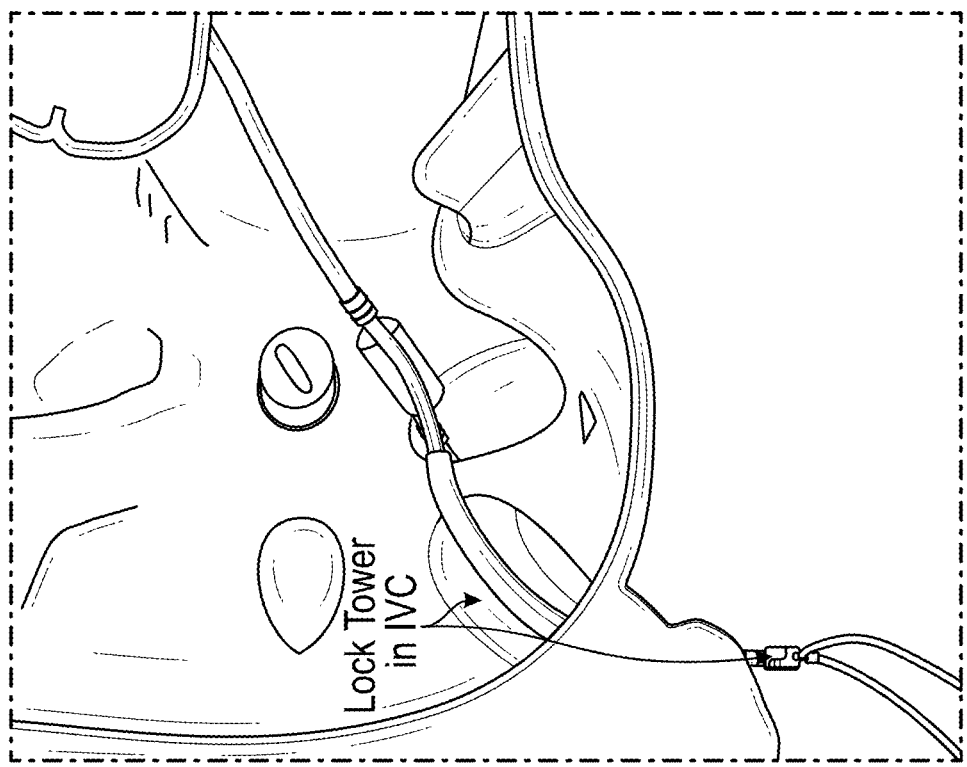
Figure 17C:
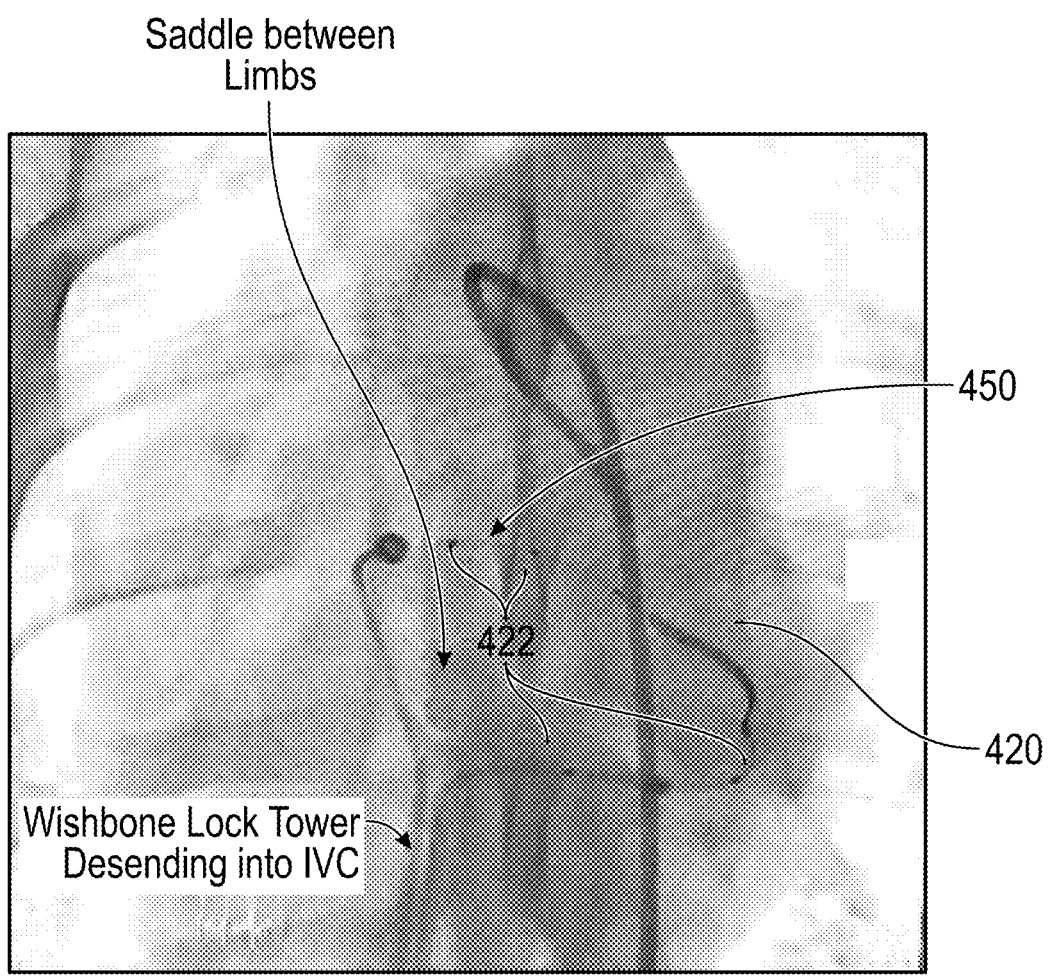
Figures 18A, 18B, 18C, 18D:
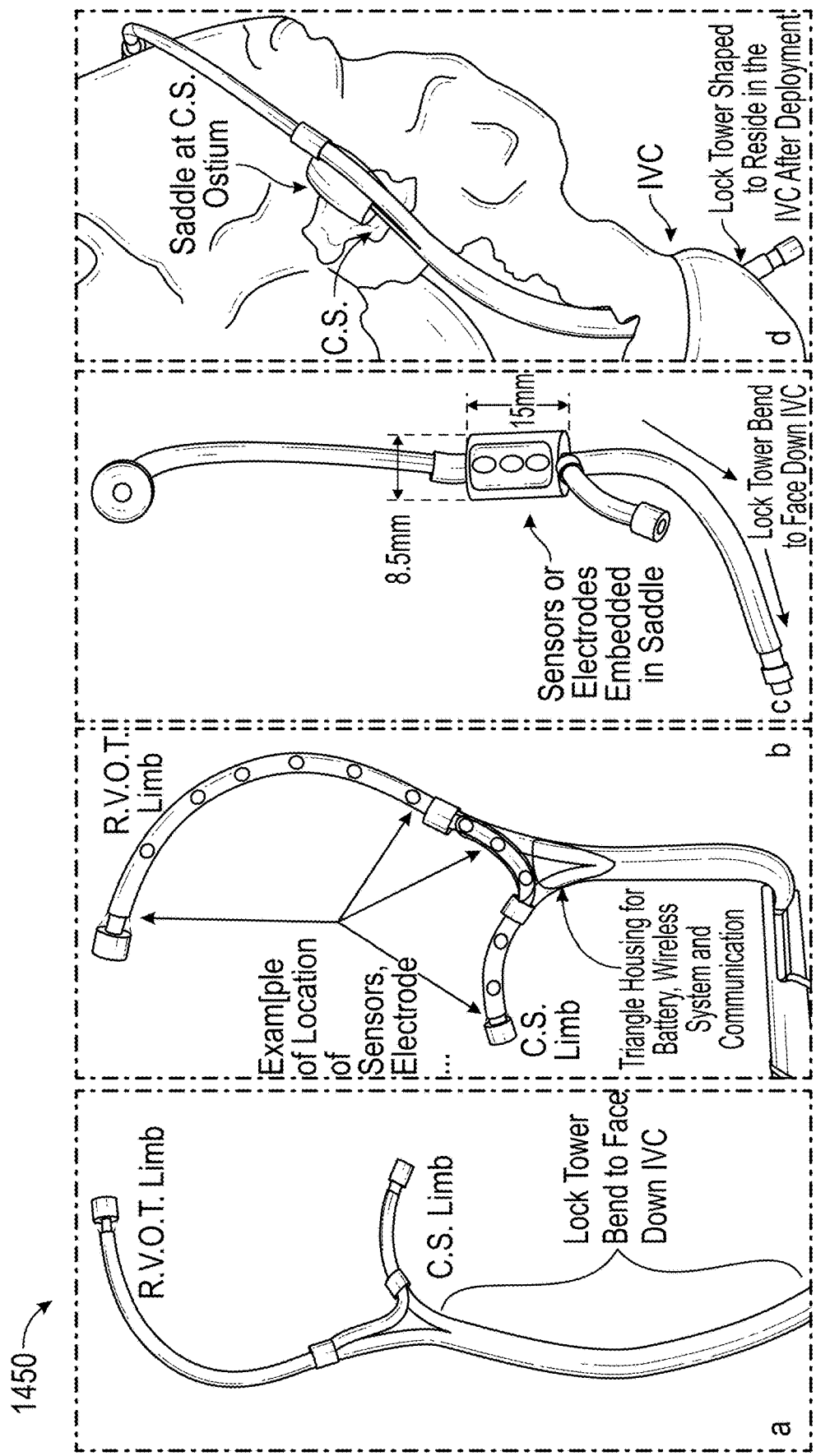
FIGS. 18A-18D illustrate further aspects of implants in accordance with the present disclosure.
Figure 19B:
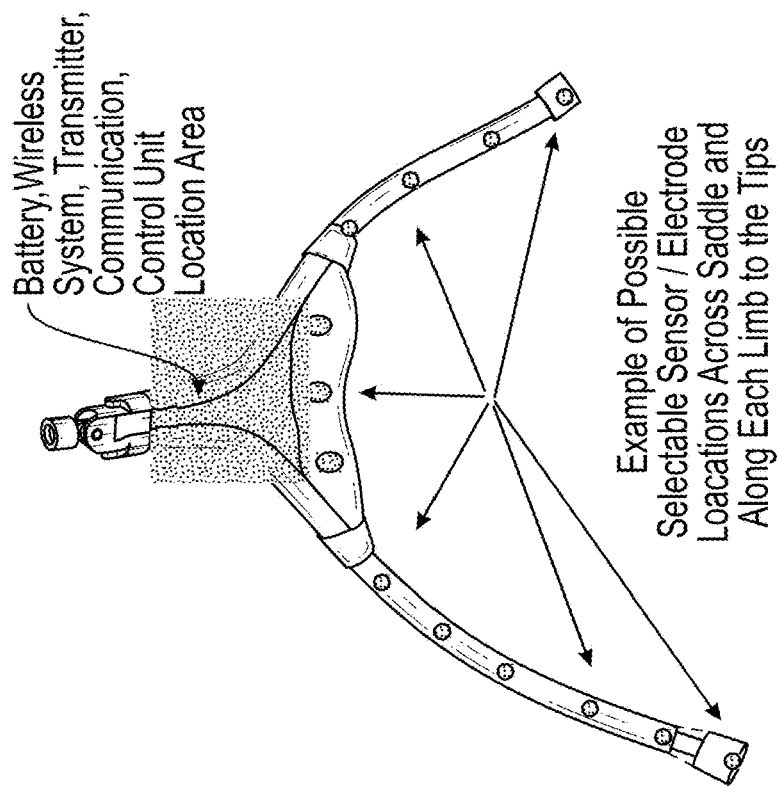
FIGS. 19A-E illustrate further aspects of implants in accordance with the present disclosure.
Figure 19A:
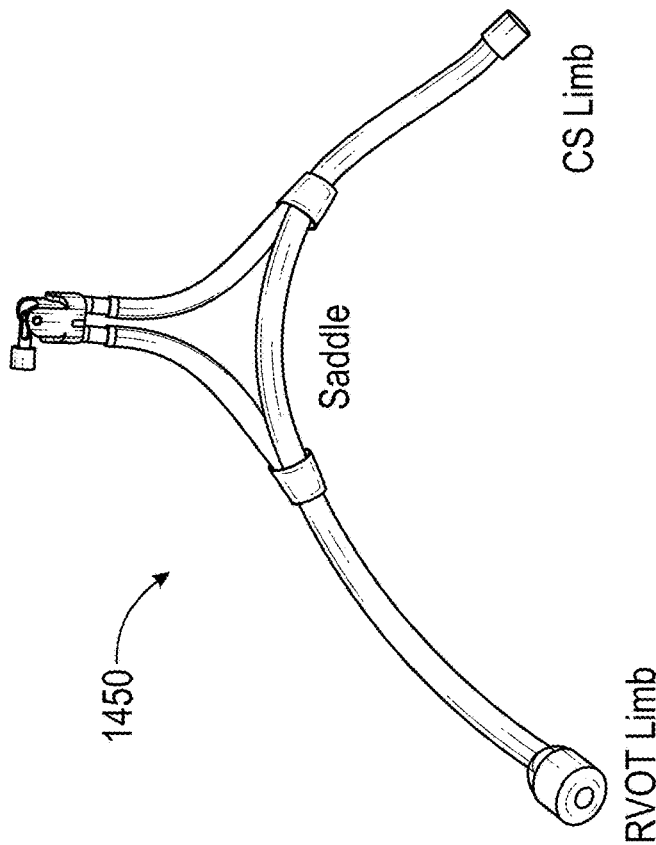
Figure 19D:
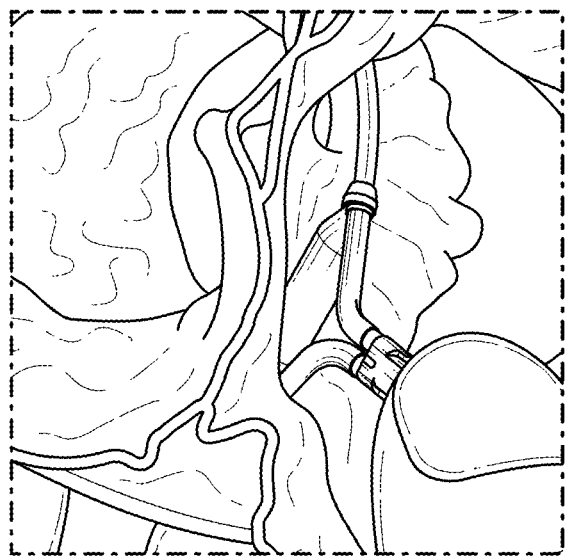
Figure 19E:
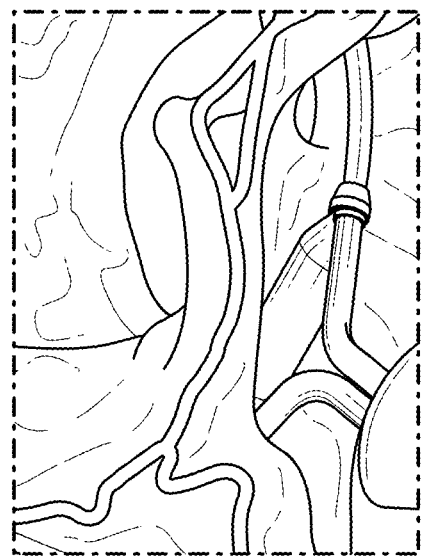
Figure 19C:
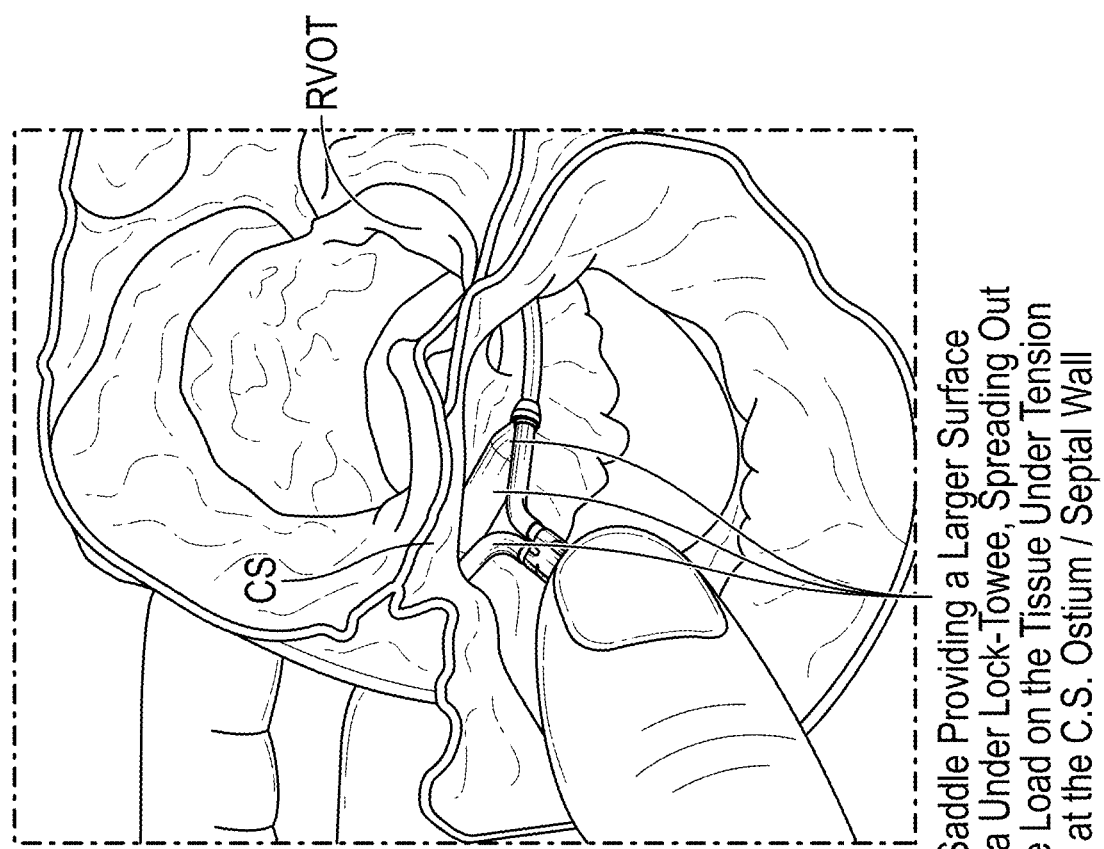

FIGS. 16A-16B illustrate further implementations of a wishbone and lock implant in accordance with the present disclosure that is configured for femoral access. FIG. 16A depicts such an implant without a saddle attachment, and FIG. 16B depicts such an implant with a saddle attachment. As with the wishbone lock of FIGS. 14A-14B, the wishbone lock depicted in FIGS. 16A-16B each include a lock body having a coronary sinus (CS) limb and right ventricular outflow tract (RVOT) limb extending from a distal end of the lock, wherein the lock body defines at least one lumen therethrough (not shown) to permit passage of the tethers 450 that also pass through the CS and RVOT limbs. The lock is locked in place using a locking catheter as described, for example, in U.S. Pat. No. 10,433,962 wherein an inner locking body is pushed or pulled into place with respect to the outer body of the lock, crushing or otherwise holding the tethers 450 in place in the lock to maintain tension on the mitral annulus. As with the embodiment of FIG. 14B, the wishbone lock depicted in FIG. 16B includes a saddle attachment that spans the two limbs at the bifurcation and limits separation of the legs when under tension. Each of the limbs may terminate in a bumper, as set forth in U.S. Pat. No. 10,433,962. The saddle helps to spread out stresses along the surface of the tissue along the right atrial septal wall when the implant is placed under tension. The wishbone lock depicted in depicted in FIGS. 16A-16B is particularly configured for performing a mitral cerclage procedure as set forth in U.S. Pat. No. 10,433,962, except by way of femoral access. The shape of the lock and wishbone is therefore configured for access from that direction. In particular, the portion of the assembly including the lock, referred to herein as the lock tower, descends into the inferior vena cava since that is the direction obtained by way of femoral access. Specifically, both limbs extend outwardly in a parallel direction. A first of the limbs then curves off laterally for introduction into the coronary sinus, and then the second RVOT limb also curves off laterally wherein the limbs both essentially turn along a perpendicular direction in order to access the CS and RVOT when using a femoral approach. As will be appreciated, the saddle can be configured to deploy in a generally planar configuration and have an effective width wider than the limbs so as to more effectively spread out tension induced stresses along the cardiac tissue. FIGS. 17A-17C illustrate views showing placement of the implant of FIGS. 16A-16B in accordance with the present disclosure. FIG. 17A depicts the relative downward placement of the lock tower of the lock assembly into the IVC upon implantation. FIG. 17B depicts the saddle of the implant of FIGS. 16A-16B disposed across the coronary sinus ostium and septal wall, and depicts the positioning of the coronary sinus limb with respect to the coronary sinus and the relative positioning of the RVOT limb through the tricuspid valve. FIG. 17C is an image depicting implantation of the device of FIGS. 16A-16B in situ in a porcine model showing the wishbone descending into the IVC and the relative location of the saddle between the limbs. Also shown are the remainder of the implant including the sheath 450 which surrounds the arched bridge 420. Also depicted are marker bands 422 spaced from each other and crimped around the tether 450 in order to help accomplish measurement and the amount of tether 450 that has been withdrawn through the limbs and the lock. FIGS. 19C-E illustrate placement of the implant of FIG. 16B in situ in a simulated cardiac structure. FIG. 19C illustrates how, with the embodiment of FIG. 16B, the saddle band that connects the CS and RVOT limbs spreads out and provides a large surface area under the lock tower to spread out the load on the tissue that is under tension.

In further accordance with the disclosure, the implants of FIGS. 14 and 16 can be used as a structure to support pacing electrodes and pacer hardware to permit cardiac pacing.

For purposes of illustration only, and not limitation, FIGS. 18A-18D illustrate further aspects of the implant of FIG. 16B in accordance with the present disclosure to show relative placement of sensors and electrodes when the device is adapted to use for pacing. FIGS. 19A-B also depict illustrative placement of sensors and other components for the implant of FIG. 14B In some implementations, an implantable pacing system configured and arranged to circumnavigate a loop path in a heart can be provided. For example, U.S. Ser. No. 15/328,046 sets forth one technique for implanting a pacemaker lead via the septal vein using an approach through the coronary sinus, in a manner similar to making a path to implant devices in accordance with the present disclosure.

Thus, an initial lead (preferably a bipolar lead) is anchored in the myocardium at a location where signals originating therefrom can provide a minimum signal. Once suitably anchored, if desired, a proximal end of the lead, or an extension thereof, can be externalized from the patient, and a specially configured implant similar in structure to those disclosed herein can be delivered over the cardiac lead, using the cardiac lead as a delivery rail at least in part. Alternatively, the cardiac lead can be externalized, and the implant can be delivered after being crimped to a proximal end of an externalized guidewire as disclosed herein, and the implant can be installed. When it comes time to install the lock, the lock can be threaded over the implant (e.g., 400) as well as the cardiac lead, and when the lock is locked in place, the lock can be configured to complete an electrical contact with the lead. For example, the lock can include a controller having a power supply and a signal generator. The inner elongate tether can also be caused to complete an electrical circuit with the lock, and appropriate control circuitry can be provided in the lock for the loop of platinum or other wire in the inner tether to function as an antenna for sending or receiving signals, or for receiving a charging pulse to charge a battery in the lock for powering the pacemaker.

However, the embodiments of FIGS. 18A-18D and 19A-B can also be configured, as indicated, to contain all of their sensors and electrodes as an integrated unit, on board. Thus, the implant can be delivered and assembled in place, and can be programmed to stimulate cardiac tissue and/or sense biological conditions (e.g., electrical mechanical and chemical conditions) within the heart.

Thus, the pacing system can include an elongate inner tether as set forth herein having a proximal end and a distal end, an outer sheath material surrounding the elongate inner tether having a proximal end and a distal end, at least one electrical conductor disposed along or within at least one of the elongate inner tether and the outer sheath, a cardiac pacing controller, which may be integrated into the lock of the implant as depicted, and may include a power source such as a battery, a pulse generator, and control circuitry operably coupled to the at least one electrical conductor, at least one cardiac pacing electrode configured and arranged to be implanted in or on top of cardiac tissue, the at least one cardiac pacing electrode being electrically coupled to the cardiac pacing controller by way of the at least one electrical conductor, and a lock securing the proximal end and distal end of the outer sheath material.

In some implementations, the lock can be coupled to the cardiac pacing controller. The at least one electrical conductor is disposed at least partially within the elongate inner tether housed within sheath 450 of the implant. If desired, the lock/controller can include one or more cardiac pacing leads routed therethrough terminating at electrodes indicated at predetermined locations as indicated in the figures, or in any other desired location. Electrical communication can be established with the cardiac pacing lead by engaging a portion of the lock. Or, the lock/controller can be pre-connected to cardiac leads and electrodes integrally formed into the curved tubular limbs of the implant depicted in FIGS. 18A-19B that connect to the lock/controller. If desired, the portion of the implant received by the lock limbs can also be provided with sensors. If desired, electrical power can be directly transferred to implant via a core platinum wire described elsewhere herein. Components integrated into the sheath portion that lays between the ends of the lock limbs, such as sensors and electrodes, can then draw power off of the core wire (e.g., 410a') in order to operate. Electrical connections between the power supply/lock and pacing electrodes or other sensors can be direct conductive pathways wherein conductors are placed between inner and outer tubular polymeric layers of the limbs attached to the lock/controller, or nested within the layers of the implant. If desired, the sensors or electrodes can be formed over the surface of the implant lock/limbs and sheath 450, whether or not a bridge is provided, and then be overlaid with an additional layer of heat shrunk polymeric tubing. If desired, that outer layer of tubing can include windows formed therein for exposing the sensors or electrodes.

In some implementations, the pacing system can further include at least one lumen along a length of the outer sheath for receiving a pacing lead, wherein the pacing system can be slid along the pacing lead into the coronary sinus. The at least one lumen can be configured to direct the pacing lead toward the cardiac pacing controller. In some embodiments, the system can include a protective bridge for spanning the LCx artery when in the coronary sinus near the septal wall as described elsewhere herein. In some embodiments, at least a portion of the cardiac pacing controller can be disposed within the outer sheath.

The pacing system can further include an electrical battery disposed within components of the lock, limbs or within the outer sheath 450. The pacing system can further include a circuit board that is at least partially disposed within the outer sheath 450 or within the lock body, for example. The pacing system can further include communications circuitry that is at least partially disposed within the outer sheath. The communications circuitry can be hard wired, and/or wireless (e.g., via Bluetooth communication).

If desired, the pacing system can further include at least one sensor circuit that is at least partially disposed within the outer sheath, the at least one sensor module including at least one sensor (e.g., sensing circuitry) for sensing at least one biological parameter. For example, the at least one sensor circuit/module can include at least one pressure sensor for detecting blood pressure, or at least one of a chemical sensor, a distance sensor, a sensor having circuitry to detect electro physiological data, a movement sensor, and a location sensor.

In some implementations, the at least one electrical conductor can terminate at the lock/controller. If desired, the system can further include at least one pacing lead (and/or electrical sensor for sensing cardiac electrical signals) formed into a surface of the outer sheath. The at least one pacing lead can be configured and arranged to interface with the Right Atrium. If desired, a further pacing lead can be configured and arranged to interface with the Right Ventricle, or a cardiac vein such as the septal vein, and be located, for example, in the regions denoted by circles in FIG. 18B spaced from one another along the CS limb and/or the RVOT limb or 18C, along the saddle. Likewise FIG. 19B depicts illustrative placement of sensors and electrodes along both the RVOT and CS limbs as well as along the saddle. In both embodiments, the triangular region defined by the saddle and CS and RVOT limbs can be used to locate a housing that includes a battery, controller, and/or communications circuitry. The loop of the implant can include a conductive member along its length that can form a loop antenna for remote charging and/or communication to an outside controller. If desired, the controller can be configured and arranged to provide at least one of pacing, defibrillation, measurement and control.

Thus, in some implementations of the pacing system the inner elongate tether can include a loop antenna that conducts signals to and from the controller. In further implementations, the pacing system (or other system) can further include a reservoir for containing a beneficial agent coupled to a dispenser controlled by the controller. For example, the beneficial agent can include a medication, a gene therapy material, and/or living cells for seeding at least one location of the heart that is damaged.

The heart's intrinsic electrical activity (i.e. the P wave or QRS complex) transmits a small electrical current (a few millivolts), through the pacemaker leads, to the pulse generator. This current can be registered or sensed by the pacemaker circuitry. The pacemaker sensing can be used to formulate a response of a pacemaker to intrinsic heartbeats. The P waves, or atrial activity, are transmitted through an atrial lead (if present) to an atrial channel of the pacemaker, and sensed as atrial activity. Ventricular activity (the QRS complex) can be transmitted through the ventricular lead (if present, such as via the septal vein) to the ventricular channel of the pacemaker, and this is sensed as ventricular activity.

For electrical activity to be transmitted from the heart to the pacemaker, a closed electrical circuit must be present, just the same as for an electrical impulse to be transmitted from the pacemaker to the heart. Thus, just as with pacing, sensing can be unipolar or bipolar. Bipolar sensing detects the intrinsic electrical activity occurring between the tip electrode and the ring electrode of the lead. Unipolar sensing detects electrical activity occurring between the tip of the lead, and the metal shell of the pulse generator. Because this is a much larger area, other electrical signals, such as might be generated by the muscles of the diaphragm or sources outside the body, are more likely to be detected (and therefore incorrectly interpreted by the pacemaker as heart beats). It is important to note that the only way the pacemaker can determine which chamber a signal originates from is by which lead transmits the signal to the pacemaker. For example, the pacemaker could interpret any electrical signal transmitted through the atrial lead to the atrial channel as a P wave, even if the signal is in fact a QRS complex large enough in amplitude to be sensed by the atrial channel. Note also that the time at which the pacemaker senses the atrial or ventricular signal is not necessarily the beginning of the P wave or QRS. The pacemaker cannot sense activity in a chamber until the electrical activity actually reaches the pacemaker lead.

Figure 20A:
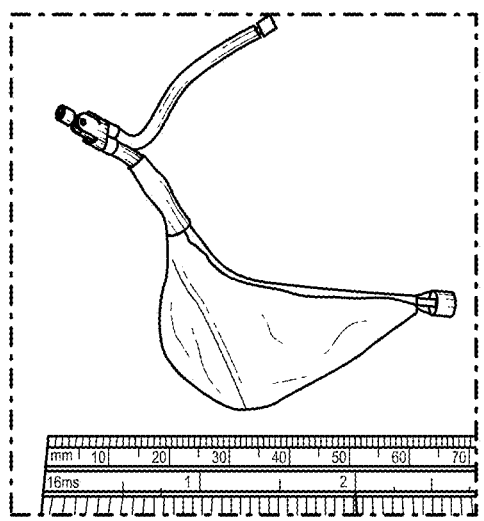
FIGS. 20A-E illustrate aspects of a leaflet structure that can be coupled to a device in accordance with the present disclosure.
Figure 20B:
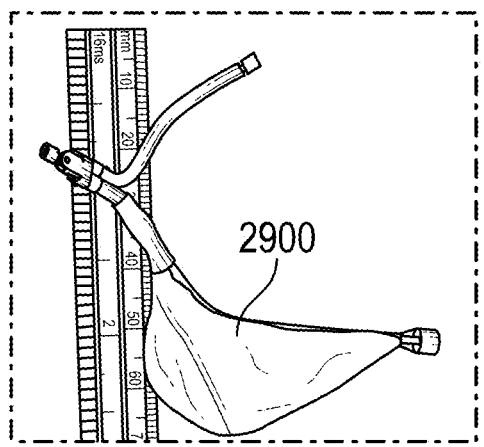
Figure 20C:
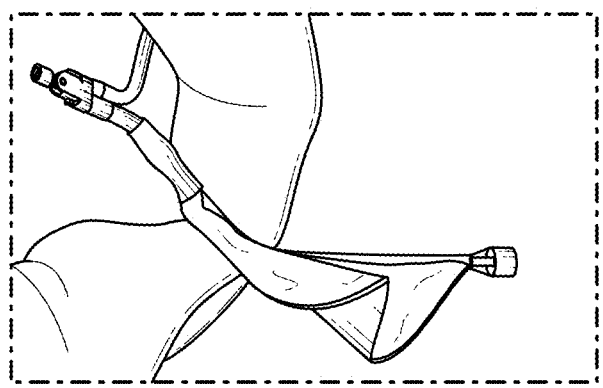
Figure 20D:
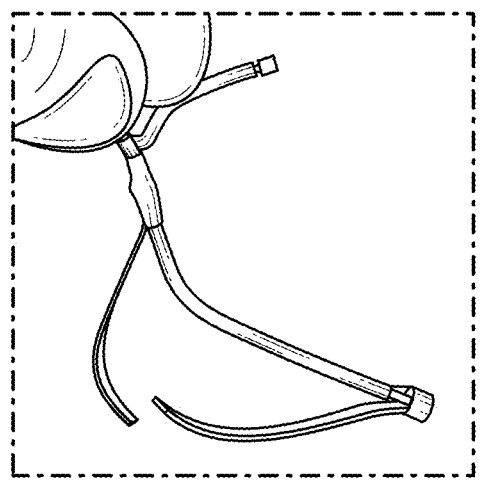
Figure 20E:
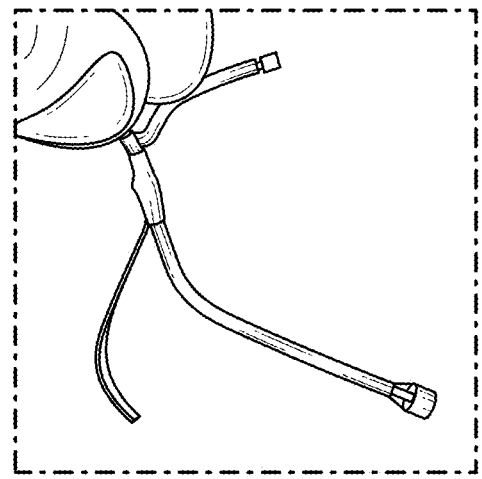
Figure 21B:
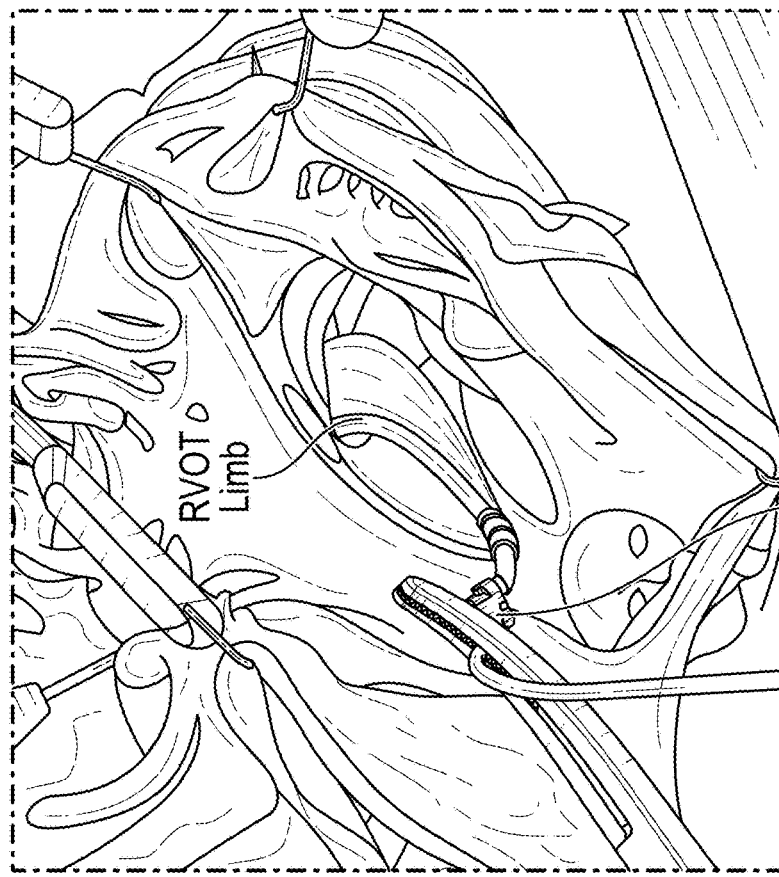
FIGS. 21A-21B illustrate placement of the implementation of FIGS. 20A-20E.
Figure 21A:
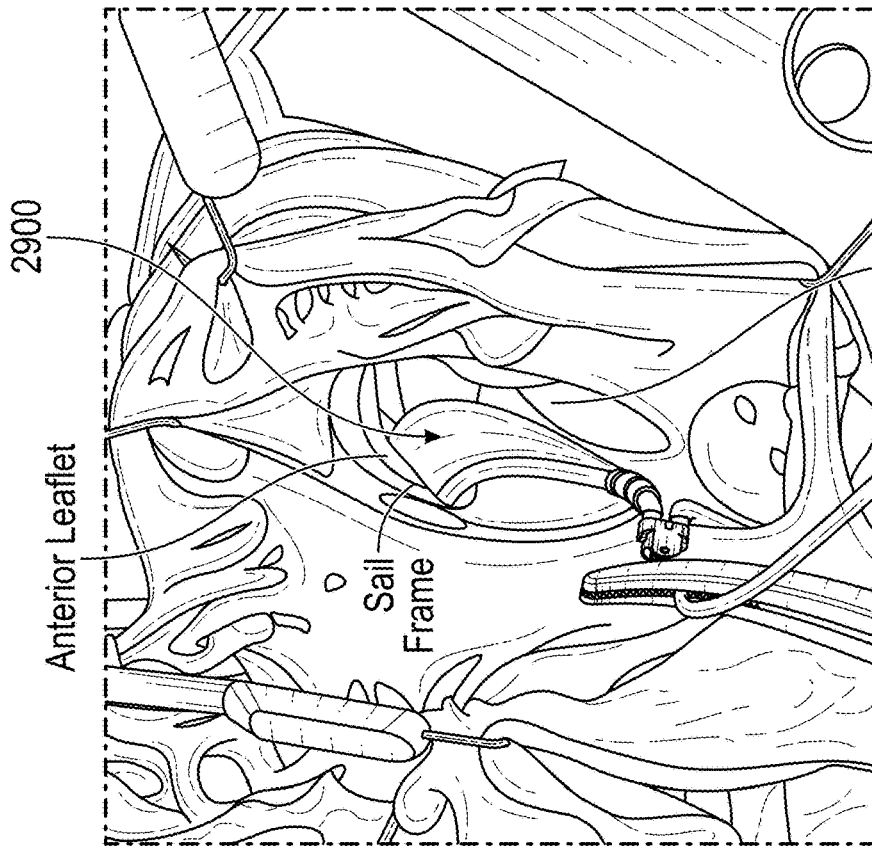

The disclosure further provides embodiments of a cardiac implant including at least one valve leaflet disposed thereon. For purposes of illustration, and not limitation, FIGS. 20A-E illustrate aspects of a leaflet structure that can be coupled to a device in accordance with the present disclosure. FIGS. 21A-21B illustrate placement of the implementation of FIGS. 20A-20E. As depicted, leaflet 2900 is preferably configured to help reduce the effects of tricuspid valve regurgitation by occupying the space between the septal tricuspid leaflet and the anterior leaflet, with the RVOT limb of the implant being located in the commissure between the leaflets. As will be appreciated, more than one sail or leaflet can be provided, as desired.

As illustrated, the RVOT limb of the lock assembly of the disclosed mitral cerclage implant may be provided with one or more deployable leaflets 2900 to complement or at least partially replace one or more native leaflets of the tricuspid valve. The leaflet 2900 can have the general shape of a sail that includes a membrane or fabric that is attached at one or more points to the RVOT limb of the mitral cerclage implant and that also includes a deployable framework. FIG. 20A illustrates such a leaflet, or sail, coupled to the RVOT limb of the mitral cerclage implant. As depicted, the leaflet has a longitudinal edge coupled to the RVOT limb. For example, the membrane or fabric can be formed into a tubular sleeve along one edge to accommodate the RVOT limb therethrough. The leaflet or sail also includes at least one free edge that can extend outwardly from the RVOT limb into the path of blood-flow in the region of the tricuspid valve. One or more deployable structural elements or ribs may be integrated with the RVOT limb, for example, by attachment thereto with a heat shrink band or other coupling, as depicted in FIGS. 20D-20E. FIG. 20D depicts two curved flattened loops of shape memory material (e.g., NiTi alloy). A distal end of a distal rib attaches near the bumper at the distal end of the RVOT limb and a proximal end of the proximal rib attaches at a proximal end or region of the RVOT limb. The sail or leaflet is preferably stitched to the structural ribs to help the leaflet to deploy when the leaflet becomes unconstrained. The sail or leaflet preferably includes inert fabric such as ePTFE, polyester, or other suitable fabric.

The leaflet can be held in a constrained position wrapped around the RVOT limb during delivery, and held in place with a binding, such as a suture (not shown) that permits the leaflet to deploy upon delivery by releasing the binding, such as by way of a slip knot or other suitable means. Alternatively, the sail can be collapsed against and/or wrapped around the RVOT limb with the CS limb and withdrawn proximally into a tubular distal end of a delivery catheter, and the sail or leaflet can self-deploy in situ when the sheath is retracted. FIGS. 21A-21B are schematics showing the placement of the sail or leaflet 2900 in situ in the RVOT proximate the tricuspid valve.

The devices and methods disclosed herein can be used for other procedures in an as-is condition, or can be modified as needed to suit the particular procedure. In view of the many possible embodiments to which the principles of this disclosure may be applied, it should be recognized that the illustrated embodiments are only preferred examples of the disclosure and should not be taken as limiting the scope of the disclosure. Each and every patent and patent application referenced herein is expressly incorporated by reference herein in its entirety for any purpose whatsoever.

The invention claimed is:

1. An implant, comprising:
 a) a tether formed into a loop shape;
 b) a lock slid over the tether and engaged with the tether to maintain tension in the tether, wherein the implant lock defines at least one distal opening therein, said at least one distal opening being connected to two distally extending tubular limbs disposed about and extending along the tether; and
 c) a spacer coupled to the lock and extending from the implant, the spacer being configured to be disposed between leaflets of a cardiac valve to permit leaflets of the cardiac valve to coapt against the spacer.

2. The implant of claim 1, wherein the tether includes an elongate inner tether and an outer sheath material, wherein the tether includes radiopaque material along its length.

3. The implant of claim 2, wherein the radiopaque material within the elongate inner tether includes a radiopaque wire disposed within a length of heat shrunk polymeric tube that resides within a hollow core of the elongate inner tether.

4. The implant of claim 1, wherein the spacer includes an inflatable member or self-expanding volume that expands to a predetermined size to occupy a portion of a patient's native tricuspid valve annulus.

5. The implant of claim 1, wherein the spacer includes a plurality of self-expanding filaments having first and second ends at proximal and distal hubs that expand radially outwardly from a compressed configuration to occupy a volume in the right ventricular outflow tract.

6. The implant of claim 1, wherein the spacer includes an elongate inflatable member configured to occupy a portion of a patient's RVOT in the region of the patient's tricuspid valve.

7. The implant of claim 6, wherein the inflatable member includes a core member coupled to first and second ends of the inflatable member.

8. The implant of claim 1, wherein the spacer is coupled to the lock by way of a further tether.

9. The implant of claim 1, wherein a first of the tubular limbs is configured to traverse the tricuspid valve and includes an atraumatic distal tip formed thereon for distributing axially applied stress across a surface of a native septum after traversing the tricuspid valve, the first tubular limb being configured to permit the outer sheath material to pass therethrough, and further wherein a second of the tubular limbs is configured to traverse the coronary sinus and is configured to permit the outer sheath material to pass therethrough.

10. An implant, comprising:
 a) an elongate tether formed into a loop shape including an outer sheath;
 b) an implant lock slid over the outer sheath and engaged with the outer sheath to maintain tension in the outer sheath material, wherein the implant lock defines at least one distal opening therein, said at least one distal opening being connected to proximal end regions of two distally extending tubular limbs disposed about the outer sheath material, wherein distal ends of the two distally extending tubular limbs extend distally away from the implant lock about the loop shape of the elongate tether and toward each other; and
 c) a saddle attached to the proximal end regions of the tubular limbs proximate the implant lock, the saddle being configured to distribute stresses over cardiac tissue when the implant is under tension.

11. The implant of claim 10, wherein the saddle is a band of material that urges against cardiac tissue when the implant is under tension.

12. An implant, comprising:
 a) an elongate tether formed into a loop shape including an outer sheath;
 b) an implant lock slid over the outer sheath and engaged with the outer sheath to maintain tension in the outer sheath material, wherein the implant lock defines at least one distal opening therein, said at least one distal opening being connected to two distally extending tubular limbs disposed about the outer sheath material; wherein:

a first of the tubular limbs is configured to traverse the coronary sinus and is configured to permit the elongate tether to pass therethrough a second of the tubular limbs is configured to traverse the tricuspid valve and configured to permit the elongate tether to pass therethrough; and the first and second tubular limbs are parallel to one another when they exit the lock, the first of the tubular limbs curves away from the second tubular limb from a point of bifurcation, and the second tubular limb then curves along a parallel path to the first tubular limb laterally separated from the first tubular limb, such that both tubular limbs point along the same direction generally orthogonal to the first direction.

13. The implant of claim 12, further comprising a saddle joining the tubular limbs near the point of bifurcation, the saddle being configured to distribute stresses over cardiac tissue when the implant is under tension.

14. The implant of claim 13, wherein the saddle is joined to the tubular limbs at least in part by way of a suture wrap.

15. The implant of claim 13, wherein the saddle is joined to the tubular limbs at least in part by way of shrink tubing.

16. The implant of claim 13, wherein the saddle is joined to the tubular limbs at least in part by way of at least partially melting material of the tubular limbs.

* * * * *